US012546055B2

(12) United States Patent
Han et al.

(10) Patent No.: US 12,546,055 B2
(45) Date of Patent: Feb. 10, 2026

(54) CLOTHING MANAGEMENT APPARATUS AND CONTROL METHOD THEREFOR

(71) Applicant: SAMSUNG ELECTRONICS CO., LTD., Suwon-si (KR)

(72) Inventors: Donggi Han, Suwon-si (KR); Hyunjoo Kim, Suwon-si (KR); Sangho Shin, Suwon-si (KR); Kwonchul Yun, Suwon-si (KR); Jungsang Choi, Suwon-si (KR)

(73) Assignee: SAMSUNG ELECTRONICS CO., LTD.

( * ) Notice: Subject to any disclaimer, the term of this patent is extended or adjusted under 35 U.S.C. 154(b) by 86 days.

(21) Appl. No.: 18/665,186

(22) Filed: May 15, 2024

(65) Prior Publication Data

US 2024/0301613 A1 Sep. 12, 2024

Related U.S. Application Data

(63) Continuation of application No. PCT/KR2022/018539, filed on Nov. 23, 2022.

(30) Foreign Application Priority Data

Jan. 6, 2022 (KR) ........................ 10-2022-0001913

(51) Int. Cl.
*D06F 58/10* (2006.01)
*D06F 58/20* (2006.01)
(Continued)

(52) U.S. Cl.
CPC .............. *D06F 58/10* (2013.01); *D06F 58/20* (2013.01); *D06F 73/02* (2013.01); *A61L 2/07* (2013.01);
(Continued)

(58) Field of Classification Search
CPC .......... D06F 58/10; D06F 58/20; D06F 73/02; D06F 58/44; D06F 2105/24;
(Continued)

(56) References Cited

U.S. PATENT DOCUMENTS

| | | | |
|---|---|---|---|
| 8,484,860 B2 | 7/2013 | Moon et al. | |
| 10,094,059 B2 | 10/2018 | Wang et al. | |

(Continued)

FOREIGN PATENT DOCUMENTS

| | | | |
|---|---|---|---|
| EP | 1586691 A2 * | 10/2005 | ............. D06F 58/20 |
| JP | 6-75394 | 10/1994 | |

(Continued)

OTHER PUBLICATIONS

International Search Report dated Feb. 28, 2023 for corresponding patent application PCT/KR2022/018539.

(Continued)

*Primary Examiner* — Benjamin L Osterhout
(74) *Attorney, Agent, or Firm* — STAAS & HALSEY LLP

(57) ABSTRACT

A clothing management apparatus, comprising: an outer case; an inner case arrangeable inside the outer case to thereby form a clothing accommodation space; a heat exchanger; and a fan. The inner case comprises: an air supply port arrangeable on the top surface of the inner case and is for supplying the air flow to the clothing accommodation space; a first exhaust port arrangeable on a side surface between the bottom surface and the top surface of the inner case; and a second exhaust port arrangeable on the bottom surface of the inner case, wherein air introduced through the first exhaust port is discharged bypassing the heat exchanger and is directed to the fan, and air introduced through the second exhaust port is discharged by passing through the heat exchanger and directed to the fan.

20 Claims, 11 Drawing Sheets

(51) Int. Cl.
*D06F 73/02* (2006.01)
*D06F 103/02* (2020.01)
*D06F 105/24* (2020.01)
*A61L 2/07* (2006.01)
*D06F 58/44* (2020.01)
*D06F 103/36* (2020.01)
*D06F 105/32* (2020.01)

(52) U.S. Cl.
CPC ............ *D06F 58/203* (2013.01); *D06F 58/44* (2020.02); *D06F 2103/02* (2020.02); *D06F 2103/36* (2020.02); *D06F 2105/24* (2020.02); *D06F 2105/32* (2020.02)

(58) Field of Classification Search
CPC ............. D06F 2105/32; D06F 2103/36; D06F 2103/02; D06F 58/203; A61L 2/07
See application file for complete search history.

(56) References Cited

U.S. PATENT DOCUMENTS

| | | | | |
|---|---|---|---|---|
| 11,035,066 | B2 * | 6/2021 | Nam | D06F 37/26 |
| 11,492,750 | B2 * | 11/2022 | Kim | D06F 58/30 |
| 11,618,991 | B2 * | 4/2023 | Shin | D06F 58/10<br>38/14 |
| 11,661,700 | B2 * | 5/2023 | Kang | D06F 58/10<br>68/5 C |
| 2012/0030960 | A1 * | 2/2012 | Ryoo | D06F 58/206<br>34/86 |
| 2021/0324566 | A1 * | 10/2021 | Oak | D06F 58/10 |

FOREIGN PATENT DOCUMENTS

| | | | | |
|---|---|---|---|---|
| JP | H08215489 | A * | 8/1996 | |
| JP | H0956992 | A * | 3/1997 | |
| JP | 2000093698 | A * | 4/2000 | |
| JP | 2002355527 | A * | 12/2002 | F24F 3/1423 |
| KR | 1019940021742 | | 2/1999 | |
| KR | 10-0658842 | | 12/2006 | |
| KR | 10-0674718 | | 1/2007 | |
| KR | 10-0764344 | | 10/2007 | |
| KR | 10-0893217 | | 4/2009 | |
| KR | 10-1265597 | | 5/2013 | |
| KR | 10-1265598 | | 5/2013 | |
| KR | 10-1312024 | | 9/2013 | |
| KR | 10-1312030 | | 9/2013 | |
| KR | 10-1463104 | | 12/2014 | |
| KR | 10-1520655 | | 6/2015 | |
| KR | 10-1736804 | | 5/2017 | |
| KR | 10-1952052 | | 2/2019 | |
| KR | 10-1954032 | | 3/2019 | |
| KR | 10-2019-0131271 | | 11/2019 | |
| KR | 10-2032910 | | 11/2019 | |
| KR | 10-2045456 | | 11/2019 | |
| KR | 10-2059911 | | 12/2019 | |
| KR | 10-2020-0021359 | | 2/2020 | |
| KR | 10-2106601 | | 5/2020 | |
| KR | 10-2020-0080962 | | 7/2020 | |
| KR | 10-2020-0081072 | | 7/2020 | |
| KR | 10-2020-0082999 | | 7/2020 | |
| KR | 10-2129614 | | 7/2020 | |
| KR | 10-2132399 | | 7/2020 | |
| KR | 10-2132400 | | 7/2020 | |
| KR | 10-2132401 | | 7/2020 | |
| KR | 10-2137205 | | 7/2020 | |
| KR | 10-2146457 | | 8/2020 | |
| KR | 10-2020-0105172 | | 9/2020 | |
| KR | 10-2162877 | | 10/2020 | |
| KR | 10-2176158 | | 11/2020 | |
| KR | 10-2020-0141226 | | 12/2020 | |
| KR | 10-2020-0142840 | | 12/2020 | |
| KR | 10-2021-0007760 | | 1/2021 | |
| KR | 10-2021-0009680 | | 1/2021 | |
| KR | 10-2021-0009689 | | 1/2021 | |
| KR | 10-2021-0009694 | | 1/2021 | |
| KR | 10-2205716 | | 1/2021 | |
| KR | 10-2021-0011699 | | 2/2021 | |
| KR | 10-2021-0012460 | | 2/2021 | |
| KR | 10-2021-0014989 | | 2/2021 | |
| KR | 10-2021-0015349 | | 2/2021 | |
| KR | 10-2021-0023168 | | 3/2021 | |
| KR | 10-2021-0026932 | | 3/2021 | |
| KR | 10-2021-0030825 | | 3/2021 | |
| KR | 10-2021-0049389 | | 5/2021 | |
| KR | 10-2021-0050222 | | 5/2021 | |
| KR | 10-2249080 | | 5/2021 | |
| KR | 10-2259365 | | 5/2021 | |
| KR | 10-2021-0063693 | | 6/2021 | |
| KR | 10-2021-0064655 | | 6/2021 | |
| KR | 10-2021-0070824 | | 6/2021 | |
| KR | 10-2021-0073939 | | 6/2021 | |
| KR | 10-2021-0077501 | | 6/2021 | |
| KR | 10-2021-0084236 | | 7/2021 | |
| KR | 10-2021-0089802 | | 7/2021 | |
| KR | 10-2021-0098214 | | 8/2021 | |
| KR | 10-2021-0106954 | | 8/2021 | |
| KR | 10-2284428 | | 8/2021 | |
| WO | WO-9321489 | A1 * | 10/1993 | F28D 15/02 |

OTHER PUBLICATIONS

Written Opinion dated Feb. 28, 2023 for corresponding patent application PCT/KR2022/018539.

* cited by examiner

CLOTHING MANAGEMENT APPARATUS AND CONTROL METHOD THEREFOR

CROSS-REFERENCE TO RELATED APPLICATIONS

This application is a continuation of International Application PCT/KR2022/018539, filed Nov. 23, 2022, and claims foreign priority to Korean Application 10-2022-0001913, filed Jan. 6, 2022, the disclosures of which are incorporated herein by reference in their entireties.

TECHNICAL FIELD

Various embodiments described herein relate to a clothing management apparatus and a method of controlling the clothing management apparatus.

BACKGROUND ART

A clothing management apparatus, which is an apparatus that cares for or manages clothes by housing them in a clothing accommodation space, may remove wrinkles, dust, or odors from the clothes or dry or sterilize the clothes. More recently, the clothing management apparatus has been provided for home use and is used to manage clothes such as shirts, pants, and coats.

For example, the clothing management apparatus may generate an air flow to clothes mounted in the clothing accommodation space using a blower fan included therein, collect dust generated from the clothes using a filter disposed in a flow path through which air flows, or discharge hot air or steam onto the clothes using a heating device.

DISCLOSURE OF INVENTION

Summary

According to an embodiment of the present disclosure, there is provided a clothing management apparatus including: an outer case forming an exterior of the clothing management apparatus; an inner case arrangeable inside the outer case to thereby form a clothing accommodation space; a heat exchanger arrangeable below a bottom surface of the inner case; and a fan arrangeable between the outer case and the inner case and adapted such that while the fan is between the outer case and the inner case, the fan induces an air flow inside the clothing accommodation space. The inner case may include: an air supply port arrangeable on a top surface of the inner case such that while the air supply port is arranged on the top surface of the inner case, the air flow is introduced to the clothing accommodation space through the air supply port; a first exhaust port arrangeable on a side surface between the bottom surface and the top surface of the inner case, such that while the first exhaust port is arranged on the side surface, air from the clothing accommodation space flows through the first exhaust port; and a second exhaust port arrangeable on the bottom surface of the inner case such that while the second exhaust port is arranged on the side surface, the air from the clothing accommodation space flows through the second exhaust port, wherein air introduced through the first exhaust port may be discharged bypassing the heat exchanger and be directed toward the fan, and air introduced through the second exhaust port may be discharged passing through the heat exchanger to be directed toward the blower fan.

According to another embodiment of the present disclosure, there is provided a method of controlling a clothing management apparatus. The method comprises driving a fan, arrangeable between an outer case of the clothing management apparatus and an inner case inside the outer case, to introduce air into a clothing accommodation space formed by the inner case; and guiding the air from the clothing accommodation space to introduce through the air to a first exhaust port and introduce the air through a second exhaust port, respectively, and separately discharging the air introduced through the first exhaust port and the air through the second exhaust port. The method may comprise collecting dust generated in the inner case as the air is introduced through the first exhaust port such that the air passes through a filter arrangeable along a first exhaust flow path, the first exhaust port being along the first exhaust flow path; heating the air introduced through the second exhaust port as the air passes through a heat exchanger arrangeable along a second exhaust flow path, the second exhaust port being along the second exhaust flow path; and receiving air from the first exhaust port and the second exhaust port and guiding the air to the fan to exhaust the air into the inner case, wherein, during the collecting of the dust, air passing through the first exhaust flow path bypasses the heat exchanger and is directed toward the fan.

DETAILED DESCRIPTION

Figure 1:
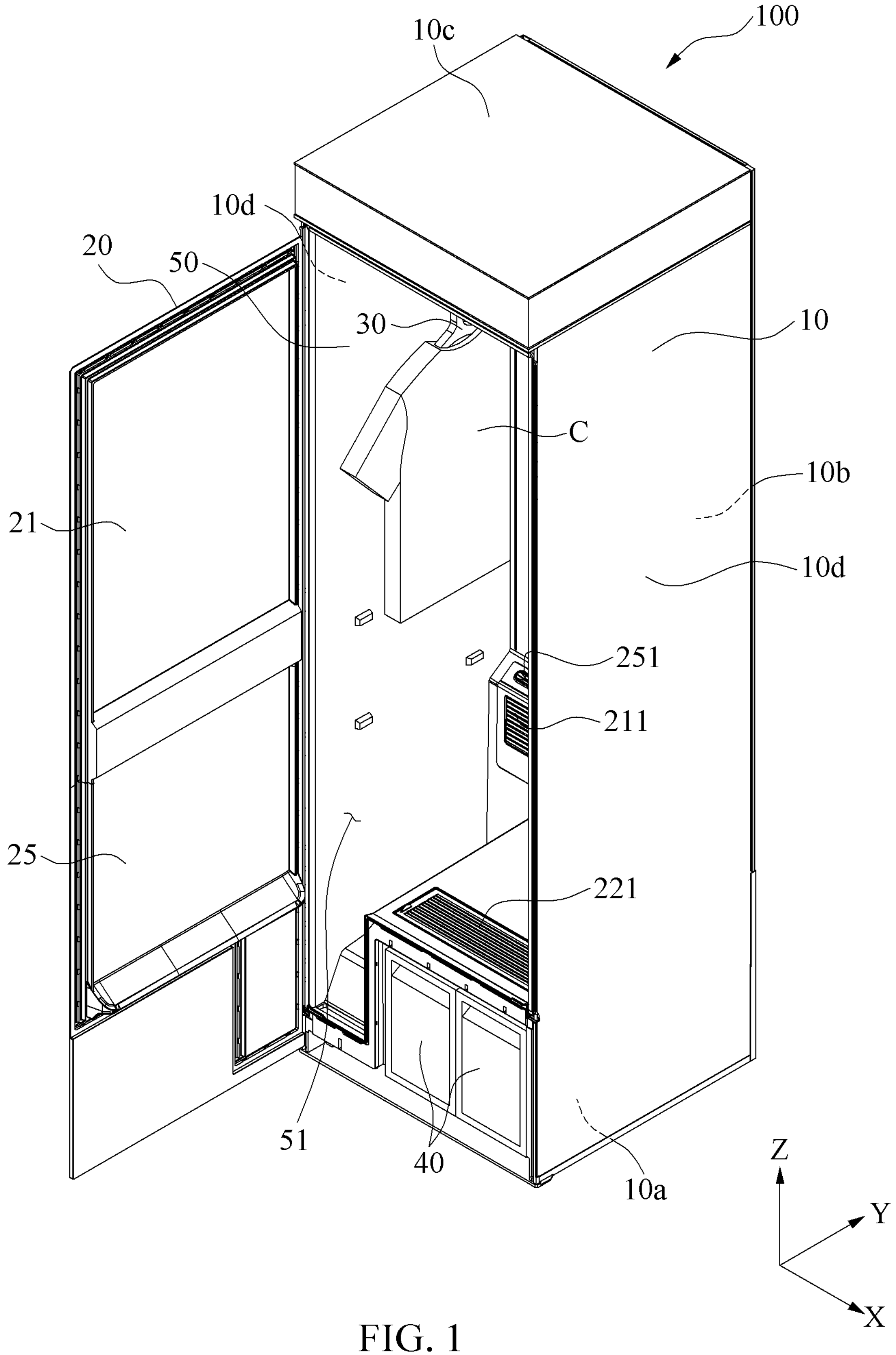
FIG. 1 is a perspective view of a clothing management apparatus according to an embodiment of the present disclosure.

Hereinafter, embodiments will be described in detail with reference to the accompanying drawings. When describing the embodiments with reference to the accompanying drawings, like reference numerals refer to like components and a repeated description related thereto will be omitted.

It should be appreciated that various embodiments of the present disclosure and the terms used therein are not intended to limit the technological features set forth herein to some particular embodiments but include various changes, equivalents, or replacements for a corresponding embodiment. In connection with the description of the drawings, like reference numerals may be used for similar or related components. It is to be understood that a singular form of a noun corresponding to an item may include one or more of the things unless the relevant context clearly indicates otherwise. As used herein, "A or B," "at least one of A and B," "at least one of A or B," "A, B or C," "at least one of A, B and C," and "A, B, or C," each of which may include any one of the items listed together in the corresponding one of the phrases, or all possible combinations thereof. Terms such as "first" or "second," or "1st" or "2nd" may simply be used to distinguish the component from other components in question, and do not limit the components in other aspects (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., by wire), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in the form of an application-specific integrated circuit (ASIC).

Various embodiments set forth herein may be implemented as software (e.g., a program) including one or more instructions that are stored in a storage medium (e.g., an internal memory or an external memory) that is readable by a machine (e.g., an electronic device). For example, at least one processor of the machine (e.g., the electronic device) may invoke at least one of the one or more instructions stored in the storage medium and execute it. This allows the machine to be operated to perform at least one function according to the at least one instruction invoked. The one or more instructions may include code generated by a complier or code executable by an interpreter. The machine-readable storage medium may be provided in the form of a non-transitory storage medium. Here, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to various embodiments, a method according to an embodiment of the disclosure may be included and provided in a computer program product. The computer program product may be traded as a product between a seller and a buyer. The computer program product may be distributed in the form of a machine-readable storage medium (e.g., a compact disc read-only memory (CD-ROM)), or be distributed (e.g., downloaded or uploaded) online via an application store (e.g., PlayStore™) or between two user devices (e.g., smartphones) directly. If distributed online, at least part of the computer program product may be temporarily generated or at least temporarily stored in the machine-readable storage medium, such as a memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components or operations may be omitted, or one or more other components or operations may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

A clothing management apparatus may include a blower fan adapted to generate an air flow and a flow path through which air is transferred, and a predetermined level or higher of air volume or air velocity may be required to secure the performance of the clothing management apparatus. Accordingly, the blower fan and the flow path may increase in size or number.

As the area occupied by the blower fan and the flow path increases, other areas of the clothing management apparatus, such as, for example, a clothing processing area, may decrease, and an area for accommodating clothes therein may decrease. In addition, in a case where a plurality of blower fans is provided, an air flow may not be evenly distributed throughout a clothing accommodation space, and air may be transferred only locally.

The technical goals to be achieved through the various embodiments disclosed herein are not limited to the technical goals described above, and other technical goals not described above may also be clearly understood by a person having ordinary skill in the art to which the present disclosure pertains from the following description.

In an embodiment, the clothing management apparatus and its control method may improve space efficiency of the clothing management apparatus, as a blower fan induces an air flow to allow air to circulate in a circulation flow path and a clothing accommodation space, and as the circulation flow path draws the air of the clothing accommodation space into a first exhaust port and a second exhaust port, separately, to allow a portion of the drawn air to pass through a heat exchanger and allow a remainder to bypass the heat exchanger.

Further, in an embodiment, the clothing management apparatus and its control method may control a travel path of air drawn from the clothing accommodation space based on a condition of the clothing accommodation space or clothes, thereby efficiently managing the clothes.

Hereinafter, various embodiments of the present disclosure will be described in detail with reference to FIGS. 1 to 11.

FIG. 1 is a perspective view of a clothing management apparatus 100 according to an embodiment of the present disclosure.

Referring to FIG. 1, the clothing management apparatus 100 according to an embodiment may include an outer case 10 and a door 20.

In an embodiment, the clothing management apparatus 100 may be a device for caring for or managing, or cleaning clothes C. The clothing management apparatus 100 may include an inner case 50 for receiving therein the clothes C and the door 20 rotatably mounted to open and close the inner case 50, and may receive the clothes C in a clothing accommodation space 51. The clothing management apparatus 100 may spray at least some of wind, hot air, steam, or fragrance onto the clothes C received in the inner case 50 to remove wrinkles, dust, or odors from the clothes C, or dry and sanitize the clothes C.

Although one embodiment of the clothing management apparatus 100 is described herein as a clothing manager installed for home use as an example, actual implementations are not limited thereto, and the clothing management apparatus 100 may be implemented as various types of clothing management apparatuses such as a drying machine or a washing machine. Hereinafter, for case of description, a target to be processed by the clothing management apparatus 100 will be referred to as "clothes C," but actual implementations are not limited thereto, and there may be various targets such as towels, blankets, or curtains.

In an embodiment, the outer case 10 may form the exterior of the clothing management apparatus 100 and, inside thereof, the inner case 50 providing the clothing accommodation space 51 receiving therein the clothes C and other components for handling the clothes C may be arranged. In an embodiment, the outer case 10 may include a first surface 10*a* in a direction (e.g., −Z direction) in which the outer case 10 faces an external support surface (e.g., ground or indoor mounted surface); a second surface 10*b* facing a direction (e.g., +Y direction) in which the outer case 10 faces the door 20 with the door 20 closed; a third surface 10*c* facing a ceiling direction (e.g., +Z direction) opposite the first surface 10*a*; and a plurality of side surfaces 10*d* in both directions (e.g., +/−X direction) extending from the first surface 10*a* to the third surface 10*c*.

In an embodiment, the door 20 may open and close the inner case 50, and when the door 20 is open, the clothes C may be placed into and removed from the clothing accommodation space 51. The door 20 may include a first door member 21 and a second door member 25 that are coupled to a side facing the clothing accommodation space 51 in a closed state. For example, the first door member 21 may include glass, a mirror, or a panel, and the second door member 25 may be a frame of the door 20, in which a door guide may be formed to guide condensate formed in the door 20. However, the structure and functions of the door 20 are not limited to the foregoing but may be implemented in various ways.

In an embodiment, the inner case 50 may include at least one support member 30 provided to hold the clothes C thereon. The support member 30 may be provided in a shape of a hanger to support the clothes C. In an embodiment, the interior of the support member 30 may be open to allow air to flow into the interior, and the air may flow into the interior of the clothes C mounted on the support member 30 to remove dust or dirt.

In an embodiment, a water reservoir 40 that is removably arranged from the outer case 10 may be provided in a direction of the first surface 10*a* of the outer case 10. The water reservoir 40 may be a water supply reservoir for supplying water to a steam generation module (e.g., a steam generation module 116 in FIG. 2) to generate steam or a drain reservoir for draining condensate generated in a heat exchanger (e.g., a heat exchanger 118 in FIG. 2) to the outside. In an embodiment, a machine chamber (e.g., a machine chamber 60 in FIG. 3) may be provided behind the water reservoir 40, and the machine chamber 60 may house various mechanical components necessary to drive the clothing management apparatus 100.

In an embodiment, inside the inner case 50, a first exhaust port 211 and a second exhaust port 221 may be provided to draw in air from the clothing accommodation space 51. The first exhaust port 211 and the second exhaust port 221 will be described in more detail below with reference to FIG. 3 and the following drawings.

Figure 2:
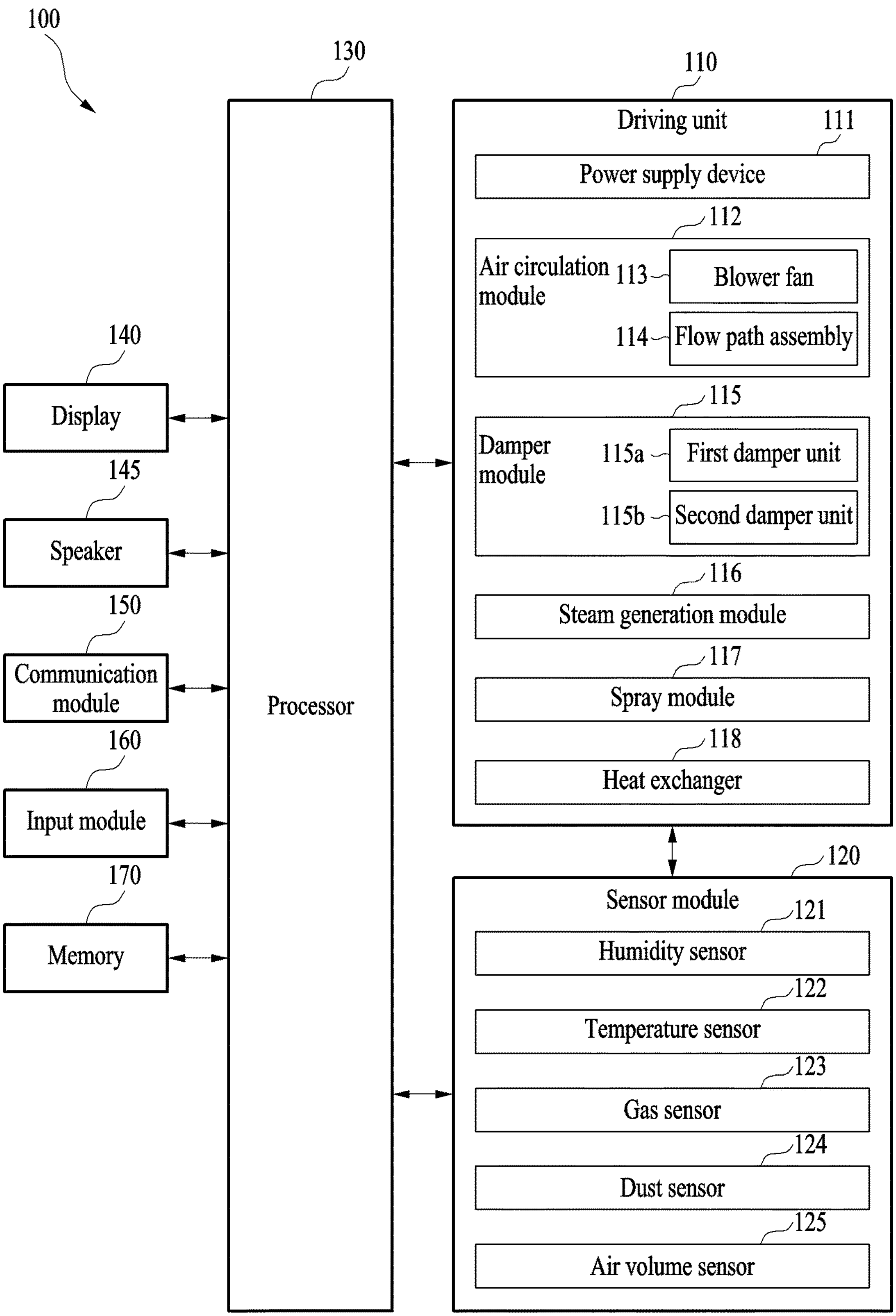
FIG. 2 is a block diagram illustrating a configuration of a clothing management apparatus according to an embodiment of the present disclosure.

FIG. 2 is a block diagram illustrating a configuration of the clothing management apparatus 100 according to an embodiment of the present disclosure.

Referring to FIG. 2, the clothing management apparatus 100 may include at least some of a driving unit 110, a sensor module 120, and at least one processor 130.

In an embodiment, the clothing management apparatus 100 may be implemented with a combination of one or more configurations or features of the previously described embodiments unless it is technically obviously impossible.

In an embodiment, the driving unit 110 may be a component provided to perform the overall mechanical operation of the clothing management apparatus 100 and may perform various operations under the control of at least one processor 130.

In an embodiment, a power supply device 111 may provide power to the driving unit 110 and other components of the clothing management apparatus 100. The power supply device 111 may provide power to a blower fan 113 and may control the driving of the blower fan 113. For example, the power supply device 111 may control the speed of the blower fan 113 using a voltage control method or a frequency conversion method according to a control signal from at least one processor 130.

In an embodiment, the power supply device 111 may be controlled by an intelligent power module (IPM) configured as a switching device. The IPM may be a power module to which a protection function for protecting a power device or a drive circuit is added. For example, the power supply device 111 adapted to control a heat exchanger 118 may prevent components of the power supply device 111 and the clothing management apparatus 100 from being damaged by overheating from an increased load.

In an embodiment, an air circulation module 112 may include the blower fan 113 and a flow path assembly 114. When the blower fan 113 is driven, the air circulation module 112 may draw in the air of the clothing accommodation space 51 and process the air to supply the processed air back to the clothing accommodation space 51.

In an embodiment, the blower fan 113 may be installed in the flow path assembly 114 and may induce an air flow in the flow path assembly 114 and the clothing accommodation space 51. In an embodiment, the flow path assembly 114 may communicate to draw in air from the clothing accommodation space 51, process the air, and discharge the processed air back into the clothing accommodation space 51. The flow path assembly 114 may allow air in the inner case 50 to circulate and may continuously apply a strong wind or hot air to clothes C received in the inner case 50. In an embodiment, the flow path assembly 114 may include at least some of a first exhaust flow path (e.g., a first exhaust flow path 210 in FIG. 4), a second exhaust flow path (e.g., a second exhaust flow path 220 in FIG. 4), and a circulation flow path (e.g., a circulation flow path 230 in FIG. 4).

In an embodiment, a damper module 115 may be movably installed inside the flow path assembly 114. The damper module 115 may increase or decrease a blowing volume of air flowing in the flow path assembly 114 while moving, and the damper module 115 may serve as an auxiliary door that opens and closes at least some areas of the flow path assembly 114.

In an embodiment, the damper module 115 may include a first damper unit 115*a* and a second damper unit 115*b* installed at different positions in the flow path assembly 114. For example, the first damper unit 115*a* may be installed in the first exhaust flow path 210 to control a flow volume of air entering an intake port (e.g., the first exhaust port 211 in FIG. 1) of the first exhaust flow path 210, and the second damper unit 115*b* may be installed in the second exhaust flow path 220 to control a flow volume of air entering an intake port (e.g., the second exhaust port 221 in FIG. 1) of the second exhaust flow path 220.

In an embodiment, the steam generation module 116 may generate steam and spray the steam onto the clothes C to remove contaminants adhering to the clothes C. For example, when steam contacts a contaminant, the contaminant may be dissolved by the steam in a hot liquid state, or the steam may condense and be collected at an outlet provided on a bottom surface of the inner case 50.

In an embodiment, the steam generation module 116 may receive water via the water reservoir 40 and heat the water to generate steam. The steam generation module 116 may transfer steam to a steam spray nozzle (e.g., a steam spray nozzle 255 in FIG. 6) through a conduit, and the steam spray nozzle 255 may spray hot steam onto the clothes C mounted in the inner case 50 through a steam spray hole (e.g., a steam spray hole 251 in FIG. 6) that is open toward the clothing accommodation space 51.

In an embodiment, a spray module 117 may also spray, into the clothing accommodation space 51, various liquids, such as, for example, steam, cleansing solution, fragrance, and the like. For example, the spray module 117 may include the steam spray nozzle 255 adapted to spray steam into the clothing accommodation space 51. Without limitation, the spray module 117 may spray a cleansing fluid to clean any residual contaminants on the clothes C or spray fragrance to deodorize or make the clothes C fragrant.

In an embodiment, the heat exchanger 118 may remove moisture from, or heat, air transferred from the clothing accommodation space 51. For example, the heat exchanger 118 may dry or heat the air passing through the heat exchanger 118 as a refrigerant condenses or expands, and may provide the dried hot air to the clothing accommodation space 51.

In an embodiment, the heat exchanger 118 may include a compressor, a condenser, an evaporator, and an expander. The heat exchanger 118 may be installed in a machine chamber between the first surface 10*a* of the outer case 10 and the inner case 50. Hereinafter, the operations of dehumidifying and heating air by the components of the heat exchanger 118 will be described in detail.

In an embodiment, the compressor may compress a refrigerant in a gaseous state to be in a high-temperature and high-pressure state and may discharge the gaseous refrigerant in the high-temperature and high-pressure state. The discharged refrigerant may be transferred to the condenser.

In an embodiment, the condenser may condense a compressed gaseous refrigerant into a liquid. The condenser may release heat to the surroundings through such a condensation process of the refrigerant. The condenser may heat air through the heat generated in the condensation process of the refrigerant. The liquid refrigerant condensed by the condenser may be transferred to the expander. The expander may expand a high-temperature and high-pressure liquid refrigerant condensed in the condenser to a low-pressure liquid refrigerant. For example, the expander may include an expansion valve adapted to regulate a pressure difference of the refrigerant.

In an embodiment, the evaporator may evaporate a liquid refrigerant expanded in the expander. As a result, the evaporator may return a low-temperature and low-pressure individual refrigerant to the compressor. The evaporator may absorb heat from the surroundings through an evaporation process in which a low-pressure liquid refrigerant is changed into a gaseous refrigerant. The evaporator may cool the air passing through the evaporator during the evaporation process. When the ambient air is cooled by the evaporator, and the temperature of the ambient air becomes lower than the dew point, and the air around the evaporator may condense.

In an embodiment, as condensation occurs around the evaporator, the absolute humidity of the air passing through the evaporator may be lowered. For example, the amount of water vapor contained in the air passing through the evaporator may be reduced. Using the condensation occurring around the evaporator, the clothing management apparatus 100 may reduce the amount of water vapor contained in the air of the clothing accommodation space 51, and may also dry and sanitize the clothes C.

In an embodiment, the sensor module 120 may sense an operating state or a surrounding environment of the clothing management apparatus 100, and generate and output electrical signals of sensing results. The sensor module 120 may transmit the electrical signals to at least one processor 130 and/or store the sensing results in a memory 170 of the clothing management apparatus 100 or in an external device. For example, the sensor module 120 may generate electrical signals or obtain data by sensing an operating state or a surrounding environment of the clothing management apparatus 100 during a dry course, and at least one processor 130 may process the signals or data received from the sensor module 120 to obtain diagnostic information.

In an embodiment, sensors included in the sensor module 120 may be implemented as physically separate devices or each of the sensors may be implemented as a single device. The sensor module 120 is not limited to being implemented as a single physical device. The sensor module 120 may transmit sensing values to at least one processor 130, and at least one processor 130 may control the operations of the clothing management apparatus 100 based on the received sensing values, store them in the memory 170 as diagnostic information, or transmit them to an external device (e.g., a server and a smartphone) via a communication module 150 to store them in the external device.

In an embodiment, the sensor module 120 may include at least some of a humidity sensor 121, a temperature sensor 122, a gas sensor 123, a dust sensor 124, and an air volume sensor 125.

In an embodiment, the humidity sensor 121 and the temperature sensor 122 may sense the humidity and temperature of the clothing accommodation space 51 of the clothing management apparatus 100, respectively, or the humidity and temperature of an environment around the clothing management apparatus 100, respectively.

In an embodiment, the humidity sensor 121 may include a hygroscopic member, such as a porous ceramic or polymeric membrane, and in this case, the hygroscopic member may absorb ambient air to detect a change in resistance or capacitance or to detect a relative humidity of ambient air based on a change in resonant frequency by a change in weight.

In an embodiment, the temperature sensor 122 may be implemented as a thermistor which is a type of resistor using a property that the resistance of a material changes with temperature, and in this case, the thermistor may have a negative temperature coefficient (NTC) characteristic by which the resistance decreases as the temperature increases and increases as the temperature decreases.

In an embodiment, the temperature sensor 122 may further include a temperature adjustment device such as a thermostat, and in this case, the thermostat may detect an amount of heat generated in the heat exchanger 118 and control the temperature of air supplied to the clothing accommodation space 51 to be maintained at a specific temperature.

In an embodiment, the gas sensor 123 and the dust sensor 124 may measure a contamination level of air. For example, the gas sensor 123 may be a volatile organic compounds (VOCs) sensor and may measure the concentration of gases such as hydrogen, hydrogen sulfide, ammonia, ethanol, carbon monoxide, methane, and propane in the air of the clothing accommodation space 51. For example, the dust sensor 124 may measure the concentration of fine dust and ultra-fine dust in the air of the clothing accommodation space 51.

In an embodiment, the air volume sensor 126 may measure an air volume of the blower fan 113, and at least one processor 130 may receive the measured air volume to control a driving force of the blower fan 113 to increase or decrease. In an embodiment, the air volume sensor 126 may measure an air volume in the flow path assembly 114 or the clothing accommodation space 51. For example, the air volume sensor 126 may measure an air volume of a portion of the flow path assembly 114, for example, the first exhaust flow path 210 or the second exhaust flow path 220, and at least one processor 130 may control a movement of the damper module 115 based on the measured air volume.

In an embodiment, the sensor module 120 is not limited to the configuration described above, but may further include at least one of a filter sensor (not shown) adapted to sense a state of a filter (e.g., a filter 212 in FIG. 4) detecting a type or remaining amount of detergent, a door sensor (not shown) adapted to sense whether the door 20 is open or closed, and a vibration sensor (not shown) adapted to sense the degree to which the clothing management apparatus 100 vibrates.

In an embodiment, at least one processor 130 may control the overall operation of the clothing management apparatus 100 and may be a printed circuit board (PCB) on which a plurality of electronic components is mounted. At least one processor 130 may include, for example, at least some of a random-access memory (RAM), a read-only memory (ROM), a graphics processing unit (GPU), a main central processing unit (CPU), first to n interfaces, and a bus.

In an embodiment, at least one processor 130 and the memory 170 may be implemented as physically separate components or as a single component in which at least one processor 130 includes the memory 170. At least one processor 130 may also be implemented as a single system configured with a single component or a plurality of components. The memory 170 may also be implemented as a single system configured with a single component or a plurality of components. The control operations of at least one processor 130 based on at least one processor 130 and the memory 170 will be described in detail below with reference to FIG. 7 and the subsequent flowcharts.

In an embodiment, when receiving a command, at least one processor 130 may operate the driving unit 110 and control the driving of the clothing management apparatus 100 such that it performs a plurality of courses in a stepwise or selective manner based on an input signal.

In an embodiment, while the clothing management apparatus 100 is being driven, the sensor module 120 may detect an operating state of the clothing management apparatus 100, and based on this, at least one processor 130 may provide feedback on the driving of the clothing management apparatus 100 or obtain diagnostic information to display it on a display 140.

In an embodiment, the display 140 may display the diagnostic information obtained through the sensor module 120 under the control of at least one processor 130. The display 140 may be disposed on the door 20 of the clothing management apparatus 100, allowing a user to check the operating state of the clothing management apparatus 100. Alternatively, the display 140 may be implemented in an external form, rather than built-in form within the clothing management apparatus 100, and may display image data on an external display that is connected, by wire or wirelessly, to the clothing management apparatus 100.

In an embodiment, a speaker 145 may be built into the clothing management apparatus 100 and may output various notifications or voice messages directly as sound, in addition to various audio data obtained through various processing operations such as decoding, amplification, noise filtering, and the like by an audio processing unit (not shown).

In an embodiment, the communication module 150 may communicate with an external device (e.g., a server and a smartphone) to transmit and receive various types of data by various types of communication methods. For example, the communication module 150 may transmit information obtained by the sensor module 120 to a server (or a smartphone), or receive control commands for driving the clothing management apparatus 100 from the server (or the smartphone).

In an embodiment, the communication module 150 may include, for example, at least one of a Bluetooth chip, a Wi-Fi chip, a wireless communication chip, and a near-field communication (NFC) chip that perform wireless communication, and an Ethernet module and a universal serial bus (USB) module that perform wired communication. In this case, the Ethernet module or USB module that performs wired communication may communicate with an external device through input/output ports.

In an embodiment, an input module 160 may be configured to receive various types of user commands from the user and transmit the received user commands to at least one processor 130. To this end, the input module 160 may include an input device such as a touch panel or key, a plurality of operation buttons, and a rotary lever.

In an embodiment, the memory 170 may store various instructions, programs, or data necessary for the operations of the clothing management apparatus 100 or at least one processor 130. The memory 170 may store information obtained by the sensor module 120 and data received from an external electronic device.

In an embodiment, the memory 170 may be accessed by at least one processor 130, and data may be read/written/modified/deleted/updated by at least one processor 130. Therefore, in describing embodiments of the present disclosure, the term "memory" may include the memory 170, a RAM or a ROM in at least one processor 130, or a memory card provided in the clothing management apparatus 100.

In an embodiment, the memory 170 may be implemented as a volatile memory such as a static random-access memory (SRAM) and a dynamic random-access memory (DRAM), a non-volatile memory such as a flash memory, a ROM, an erasable programmable read-only memory (EPROM), and an electrically erasable programmable read-only memory (EEPROM), a hard disk drive (HDD), or a solid-state drive (SSD).

Figure 3:
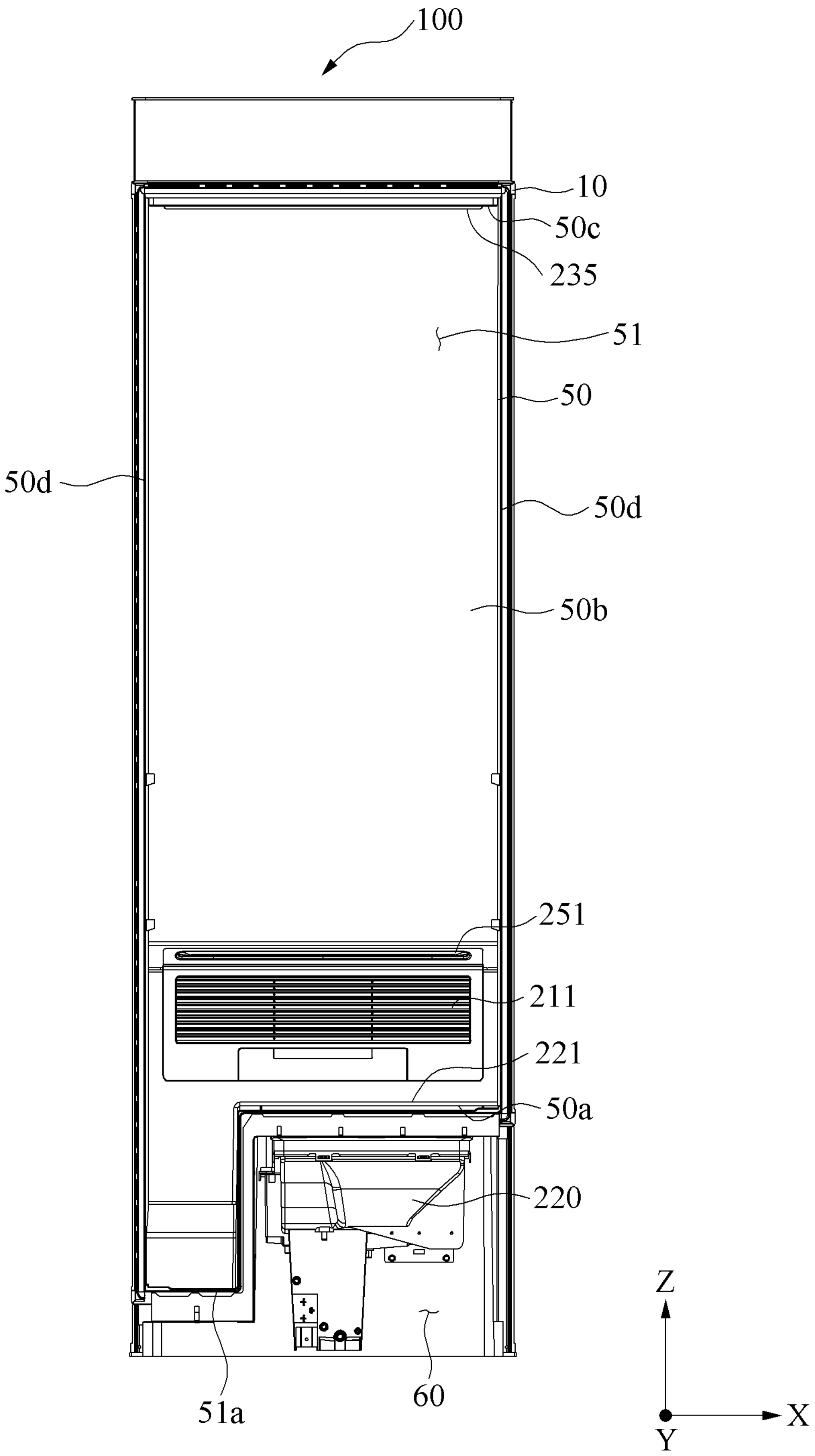
FIG. 3 is a front view of a clothing management apparatus according to an embodiment of the present disclosure.
Figure 4:
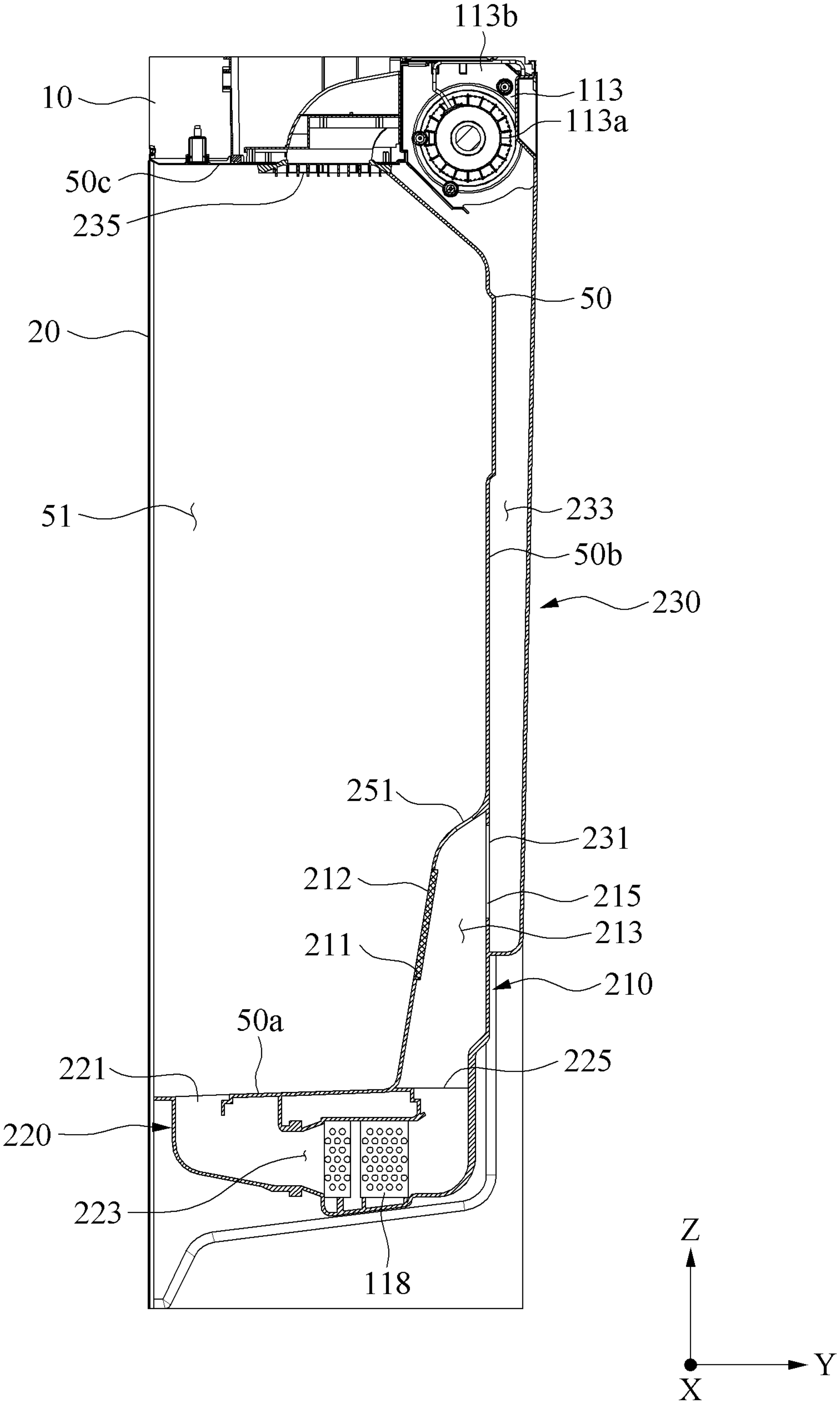
FIG. 4 is a side view of a clothing management apparatus according to an embodiment of the present disclosure.

FIG. 3 is a front view of the clothing management apparatus 100 according to an embodiment of the present disclosure, and FIG. 4 is a side view of the clothing management apparatus 100 according to an embodiment of the present disclosure.

Referring to FIGS. 3 and 4, the clothing management apparatus 100 according to an embodiment may include a first exhaust flow path 210, a second exhaust flow path 220, and a circulation flow path 230.

In an embodiment, the clothing management apparatus 100 may be implemented with a combination of one or more configurations or features of the previously described embodiments unless it is technically obviously impossible.

In an embodiment, the inner case 50 may form the clothing accommodation space 51 inside thereof and may include a first surface 50*a* that is a bottom surface; a second surface 50*b* that is one side facing the door 20 with the door 20 closed; a third surface 50*c* that is a top surface facing the first surface 50*a*; and a plurality of side surfaces 50*d* in both directions (e.g., +/−X direction) extending from the first surface 50*a* to the third surface 50*c*.

In an embodiment, the first surface 50*a* of the inner case 50 may be one surface disposed adjacent to a first surface (e.g., the surface 10*a* in FIG. 1) of the outer case 10, the second surface 50*b* of the inner case 50 may be one surface disposed adjacent to a second surface (e.g., the surface 10*b* in FIG. 1) of the outer case 10, and the third surface 50*c* of the inner case 50 may be one surface disposed adjacent to a third surface (e.g., the surface 10*c* in FIG. 1) of the outer case 10.

In an embodiment, a machine chamber 60 may be provided between the first surface 50*a* of the inner case 50 and the outer case 10. The machine chamber 60 may house various components of a driving unit (e.g., the driving unit 110 in FIG. 2) for driving the clothing management apparatus 100.

In an embodiment, the machine chamber 60 may be provided restrictively below a portion (e.g., the first surface 50*a*) of the bottom surface of the inner case 50, and the bottom surface of the inner case 50 may extend to an area 51*a* where the machine chamber 60 is not formed. The inner case 50 may have an extended space of the inner case 50 including the area 51*a* extending in a vertical direction (e.g., +/−Z direction), and the area 51*a* may accommodate therein clothes C that is long such as a coat.

In an embodiment, a flow path assembly (e.g., the flow path assembly 114 in FIG. 2) may be formed in a space between the outer case 10 and the inner case 50 of the clothing management apparatus 100. The flow path assembly 114 may receive air from the clothing accommodation space 51 formed inside the inner case 10 and discharge the air into the clothing accommodation space 51 to circulate air in the clothing accommodation space 51.

In an embodiment, the flow path assembly 114 may include a first exhaust flow path 210, a second exhaust flow path 220, and a circulation flow path 230. For example, the first exhaust flow path 210 and the second exhaust flow path 220 may be flow paths located adjacent to the first surface 50*a* of the inner case 50 and adapted to draw in air from the clothing accommodation space 51, and the circulation flow path 230 may be a flow path located adjacent to the second surface 50*b* or the third surface 50*c* and adapted to exhaust air into the clothing accommodation space 51.

In an embodiment, the first exhaust flow path 210 may include a first exhaust port 211 open to the clothing accommodation space 51 to draw in air from the clothing accommodation space 51 separately, and the second exhaust flow path 220 may include a second exhaust port 221 open to the clothing accommodation space 51 to draw in air from the clothing accommodation space 51 separately.

For example, a portion of the air in the clothing accommodation space 51 may be drawn through the first exhaust port 211, and the remainder of the air in the clothing accommodation space 51 may be drawn through the second exhaust port 221. At least some of the first exhaust port 211 and the second exhaust port 221 may be formed on the first surface 50*a* of the inner case 50 or may be formed at a position relatively adjacent to the first surface 50*a* compared to the third surface 50*c*.

In an embodiment, the circulation flow path 230 may be formed between the outer case 10 and the inner case 50, and may be disposed, for example, between the second surface 50*b* of the inner case 50 and the outer case 10. The circulation flow path 230 may receive air from the first exhaust flow path 210 and the second exhaust flow path 220 and exhaust the air into the clothing accommodation space 51. In an embodiment, an air supply port 235 of the circulation flow path 230 may be formed on the third surface 50*c* of the inner case 50 to exhaust air in a direction from the third surface 50*c* to the inner case 50.

In an embodiment, the first exhaust flow path 210 may include the first exhaust port 211, a first flow path space 213 through which air drawn in the first exhaust port 211 flows, and a first intermediate opening 215 into which air that has passed through the first flow path space 213 is exhausted.

In an embodiment, the first exhaust port 211 of the first exhaust flow path 210 may be open to be inclined at a predetermined angle in a direction from the first surface 50*a* to the second surface 50*b* to allow air to be drawn therein from the clothing accommodation space 51. In an embodiment, the air supply port 235 of the circulation flow path 230 may discharge air in a downward direction (e.g., −Z direction) from the third surface 50*c*, and thus the first exhaust port 211 disposed to be inclined may be advantageous in drawing in air that flows downward.

In an embodiment, the air exhausted from the clothing accommodation space 51 through the first exhaust port 211 may bypass the heat exchanger 118 or detour around the heat exchanger 118 to be directed toward the blower fan 113. In an embodiment, the first exhaust port 211 may be separated or partitioned from the second exhaust port 221 to draw air from the clothing accommodation space 51, and the air exhausted through the second exhaust port 221 may pass through the heat exchanger 118 to be directed to the blower fan 113.

In an embodiment, a filter 212 may be provided in the first exhaust flow path 210 and adapted to collect dust from the air drawn in the first exhaust port 211. In an embodiment, the filter 212 may be installed in the first exhaust port 211 or in the first flow path space 213 and adapted to filter out dust or fine dust generated in the inner case 50. In an embodiment, the filter 212 may be a filter of various types, and may filter out at least some of, for example, dust, fine dust, ultra-fine dust, bacteria, polymeric materials, or viruses.

For example, the flow path assembly 114 may exhaust air toward the inner case 50, and the exhausted air may dislodge, from the clothes C, debris or dirt adhering to the clothes C mounted in the inner case 50. Of the debris, relatively light dust or fine dust may move along with air. At least a portion of the air in the inner case 50 may be drawn into the first exhaust port 211 and may be filtered out as it passes through the filter 212.

In an embodiment, the first exhaust port 211 may have a shape extending in a horizontal direction (e.g., +/−Y direction) and may have a relatively larger area compared to the second exhaust port 221 connected to the machine chamber 60. The filter 212 may be installed in the first exhaust port 211, and the size of the filter 212 may correspond to the size of the first exhaust port 211.

In an embodiment, in a case where the first exhaust port 211 and the first flow path space 213 have a structure inclined relative to the first surface 50*a*, the filter 212 of a relatively large size may be provided, and an internal area of the inner case 50 may be secured. Therefore, the clothing management apparatus 100 of an embodiment may have improved dust removal performance and may be advantageous for accommodating clothes C of larger sizes or more clothes C.

In an embodiment, the first intermediate opening 215 may communicate with the circulation flow path 230. The air that has passed through the first exhaust flow path 210 may be transferred directly to the circulation flow path 230, and the air that has passed through the circulation flow path 230 may be exhausted back into the clothing accommodation space 51. The first exhaust flow path 210 and the circulation flow path 230 may circulate air in the clothing accommodation space 51.

In an embodiment, the second exhaust flow path 220 may include the second exhaust port 221, a second flow path space 223 through which air drawn in from the second exhaust port 221 flows, and a second intermediate opening 225 into which air that has passed through the second flow path space 223 is exhausted.

In an embodiment, the second exhaust port 221 of the second exhaust flow path 220 may be open in a direction (e.g., X-Y plane direction) substantially parallel to the first surface 50*a*. Without limitation, the second exhaust port 221 may be open to be inclined in a direction from the clothing accommodation space 51 to the machine chamber 60. In an embodiment, the second exhaust flow path 220 may be a housing that houses or supports internal components of the machine chamber 60.

In an embodiment, the heat exchanger 118 may communicate with the second exhaust flow path 220 and may heat and/or dehumidify the air drawn in the second exhaust port 221. In an embodiment, the heat exchanger 118 may be installed in or communicate with the second flow path space 223 and may heat and/or dehumidify the received air to discharge the air to the air supply port 235.

For example, the air that has passed through the second exhaust flow path 220 may be heated and dehumidified to be in a hot dry state, and such hot dry air may pass through the circulation flow path 230 to be discharged to the clothing accommodation space 51. The hot dry air may remove wrinkles from the clothes C or sanitize the clothes C, dry the wet clothes C, or remove water formed by steam sprayed onto the clothes C.

In an embodiment, the second intermediate opening 225 may communicate with the first exhaust flow path 210, and the second exhaust flow path 220 may communicate with the circulation flow path 230 via the first exhaust flow path 210. The air that has passed through the second exhaust flow path 220 may be transferred to the first exhaust flow path 210, and the air that has passed through the first exhaust flow path 210 may be transferred to the circulation flow path 230 to be exhausted back into the clothing accommodation space 51. The first exhaust flow path 210, the second exhaust flow path 220, and the circulation flow path 230 may circulate air in the clothing accommodation space 51. Without limitation, the second intermediate opening 225 of an embodiment may communicate with the circulation flow path 230 and may exhaust the heated and/or dried air directly through the circulation flow path 230 into the clothing accommodation space 51.

In an embodiment, the circulation flow path 230 may include an intake port 231, a circulation flow path space 233 through which air drawn in the intake port 231 flows, and the air supply port 235 into which air that has passed through the circulation flow path space 233 is exhausted. In an embodiment, the intake port 231 of the circulation flow path 230 may communicate with the first intermediate opening 215 of the first exhaust flow path 210.

In an embodiment, the air supply port 235 of the circulation flow path 230 may communicate with the inner case 50, and the air supply port 235 may be open in a direction (e.g., X-Y plane direction) substantially parallel to the third surface 50*c*. The air supply port 235 may discharge air toward the clothes C or the support member 30 mounted in the clothing accommodation space 51 of the inner case 50. In an embodiment, at least a portion of the air supply port 235 may communicate with a center of the support member 30, and the center of the support member 30 may have an open structure, and thus air exhausted into the air supply port 235 may move into the inside of the clothes C mounted on the support member 30.

In an embodiment, the circulation flow path 230 may be connected to the blower fan 113. In an embodiment, the blower fan 113 may include a fan 113*a* that rotates about a rotation axis (e.g., X-axis) and a fan housing 113*b* that houses the fan 113*a* and is installed in the circulation flow path space 233 of the circulation flow path 230 to allow air to flow therein. The fan housing 113*b* may be a component of the circulation flow path 230, and the fan 113*a* may generate an air flow in the flow path assembly 114 and the inner case 50.

In an embodiment, the circulation flow path 230 may draw in the air toward the first surface 50*a* of the inner case 50 and guide the air toward the third surface 50*c* of the inner case 50, and the circulation flow path 230 may be disposed in a direction (e.g., +Z direction) substantially parallel to the second surface 50*b* of the inner case 50 to guide the air in a direction from the first surface 50*a* of the inner case 50 to the third surface 50*c*.

Figure 5:
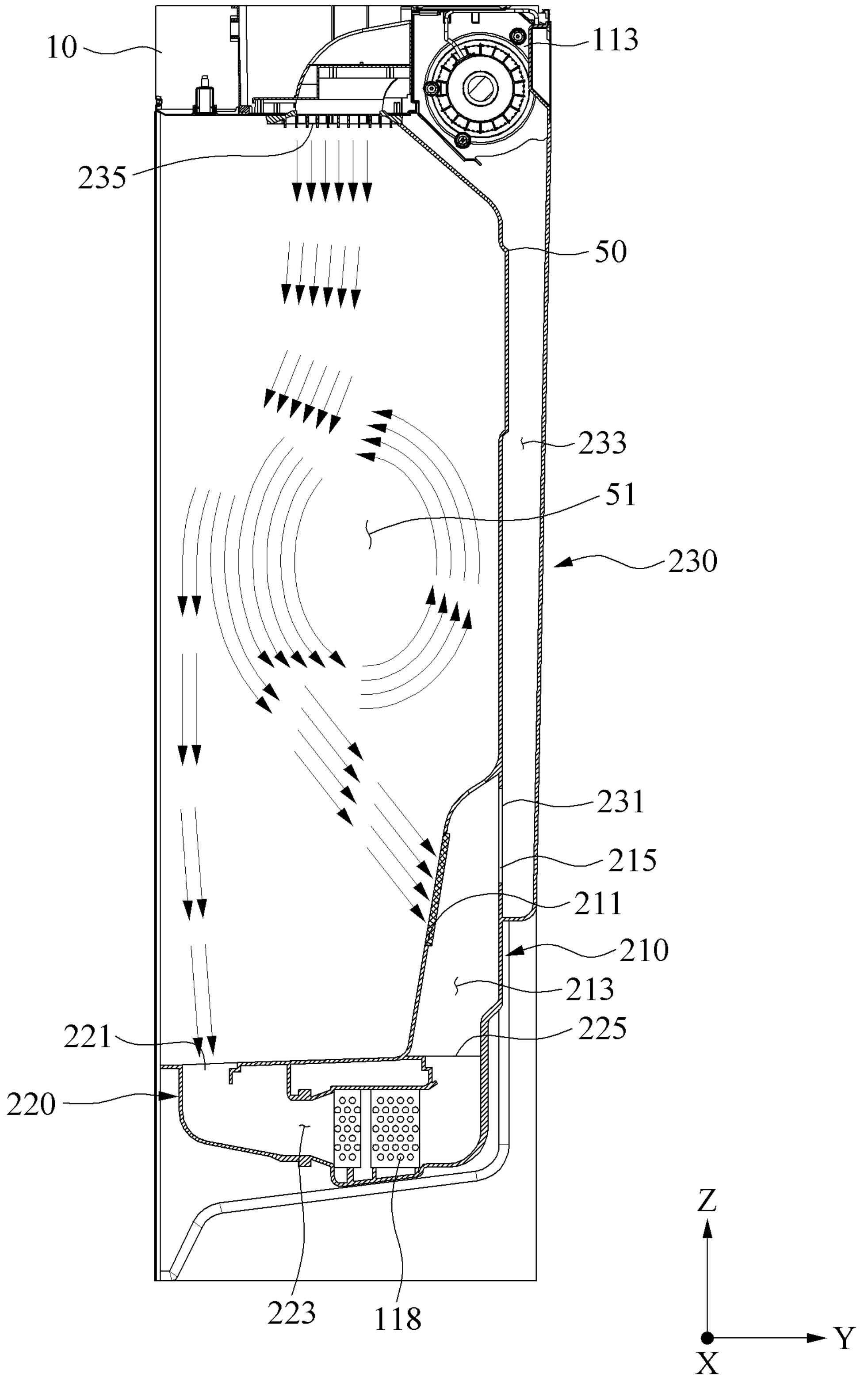
FIG. 5 is a diagram illustrating an air flow in a clothing management apparatus according to an embodiment of the present disclosure.

FIG. 5 is a diagram illustrating an air flow in the clothing management apparatus 100 according to an embodiment of the present disclosure.

Referring to FIG. 5, an air circulation structure of the flow path assembly 114 and the inner case 50 of the clothing management apparatus 100 according to an embodiment is shown.

In an embodiment, the clothing management apparatus 100 may be implemented with a combination of one or more configurations or features of the previously described embodiments unless it is technically obviously impossible.

In an embodiment, the blower fan 113 may generate an air flow in the circulating flow path 230 of the flow path assembly 114 and the clothing accommodation space 51. The blower fan 113 may be disposed adjacent to the air supply port 235, and the air supply port 235 may discharge air at a relatively high air pressure. At least a portion of the air discharged from the air supply port 235 may circulate in the clothing accommodation space 51, and the air in the clothing accommodation space 51 may be drawn into one of the first exhaust port 211 and the second exhaust port 221.

In an embodiment, the flow path assembly 114 may divide and draw in air from the clothing accommodation space 51 through the first exhaust port 211 and the second exhaust port 221, separately. At least a portion of the air drawn in separately may be dusted off, and the dust-free air may bypass the heat exchanger 118 to be supplied to the clothing accommodation space 51, while the remainder of the air drawn in separately may pass through the heat exchanger 118 to be heated and supplied to the clothing accommodation space 51.

In an embodiment, a ratio of air to be transferred to the first exhaust port 211 and the second exhaust port 221 may be adjusted to a preset ratio based on an operation of the clothing management apparatus 100. In an embodiment, at least one processor 130 may control the properties of air to be exhausted into the clothing accommodation space 51 based on a plurality of courses.

In an embodiment, at least one processor 130 may control the driving of the first damper unit 115*a* and the second damper unit 115*b* to regulate a flow volume ratio of air entering the first exhaust port 211 and the second exhaust port 221 based on the plurality of courses.

For example, based on a reference value of "9.3" for a flow volume of air exhausted from the air supply port 235 per unit time, when both the first exhaust port 211 and the second exhaust port 221 are open, a ratio of respective flow volumes per unit time of air transferred to the first exhaust port 211 and the second exhaust port 221 may be 7:2.3 (e.g., the first exhaust port 211: the second exhaust port 221).

In an embodiment, the damper module 115 may restrict a flow of air entering the first exhaust port 211 and the second exhaust port 221 or may close one of the first exhaust port 211 and the second exhaust port 221, and at least one processor 130 may control the damper module 115 to regulate the ratio of air entering the first exhaust port 211 and the second exhaust port 221. In an embodiment, how at least one processor 130 controls the flow volume of the first exhaust port 211 and the second exhaust port 221 will be described in more detail below with reference to FIG. 8 and subsequent drawings.

Figure 6:
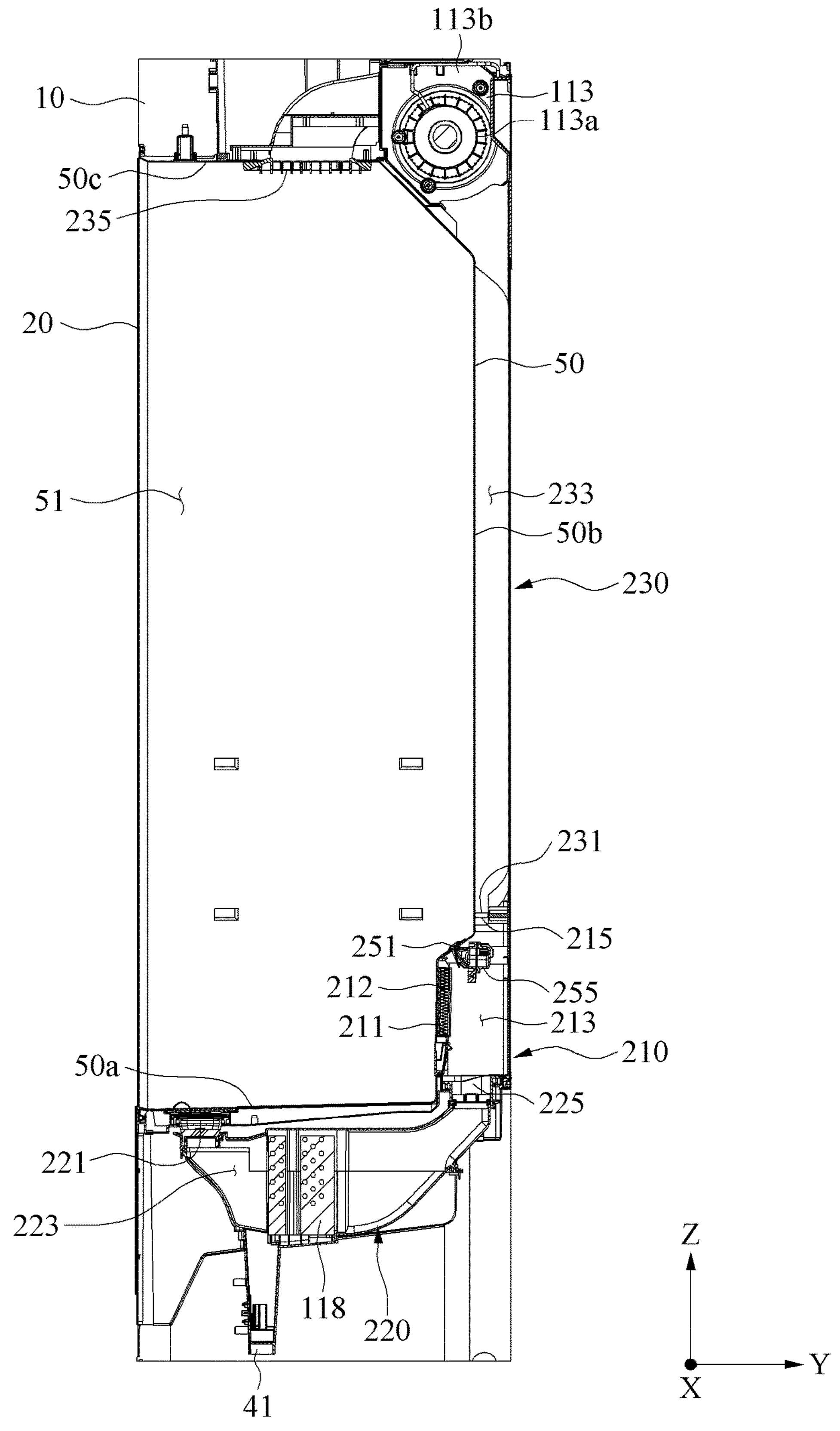
FIG. 6 is a side view of a clothing management apparatus according to an embodiment of the present disclosure.

FIG. 6 is a side view of the clothing management apparatus 100 according to an embodiment of the present disclosure.

Referring to FIG. 6, the clothing management apparatus 100 according to an embodiment may include a steam spray nozzle 255. FIG. 6 illustrates an embodiment of the clothing management apparatus 100 with some modifications to the structure of the clothing management apparatus 100 described above, and a repeated description thereof will be omitted.

In an embodiment, the clothing management apparatus 100 may be implemented with a combination of one or more configurations or features of the previously described embodiments unless it is technically obviously impossible.

In an embodiment, the steam spray nozzle 255 may be disposed inside the first exhaust flow path 210 and may spray steam into the clothing accommodation space 51 through a steam spray hole 251 formed in the first exhaust flow path 210. In an embodiment, the steam spray hole 251 may be formed on the first exhaust port 211, on the surface 50*b* of the inner case 50.

In an embodiment, the steam spray nozzle 255 and the steam spray hole 251 may be disposed to be inclined in a direction (e.g., +Z direction) from the first exhaust flow path 210 to an upper portion of the inner case 50 and may spray high-temperature and/or high-pressure steam toward the clothes C mounted in the clothing accommodation space 51 of the inner case 50.

In an embodiment, the second exhaust flow path 220 may include a connection member 41 that connects the machine chamber 60 and the water reservoir 40. For example, the connection member 41 may be connected to the steam generation module 116 from the water reservoir 40 to supply water, and may be connected to the heat exchanger 118 to drain condensate generated in the heat exchanger 118 to the water reservoir 40.

In an embodiment, the first exhaust port 211 of the first exhaust flow path 210 may be disposed in a direction substantially parallel to the second surface 50*b* to draw air from the clothing accommodation space 51. In an embodiment, the first intermediate opening 215 of the first exhaust flow path 210 and the intake port 231 of the circulation flow path 230 may be connected in a vertical direction (e.g., +Z direction).

In an embodiment, the first exhaust flow path 210 may draw air from the clothing accommodation space 51 in a horizontal direction (e.g., +Y direction) and may exhaust the air into the circulation flow path 230 in a vertical direction. For example, the first exhaust flow path 210 may receive air from the second exhaust flow path 220 in the vertical direction (e.g., +Z direction), and the air may be combined with air drawn into the first exhaust port 211 to be guided into the circulation flow path 230.

In an embodiment, when the first exhaust port 211 is disposed substantially parallel to the second surface 50*b*, a range of angles by which air travels and changes its direction from the first exhaust port 211 to the first intermediate opening 215 may be relatively reduced, and the first exhaust flow path 210 may thus be designed to be small.

In an embodiment, when a space occupied by the first exhaust flow path 210 is reduced, a space of the inner case 50 may be relatively broadened to accommodate more clothes C or clothes C of larger size. Alternatively, in an embodiment, when an angle by which air changes its direction inside the flow path assembly 114 is reduced, power consumed by the blower fan 113 of the clothing management apparatus 100 may be reduced, and/or noise generated by the clothing management apparatus 100 may be reduced.

Figure 7:
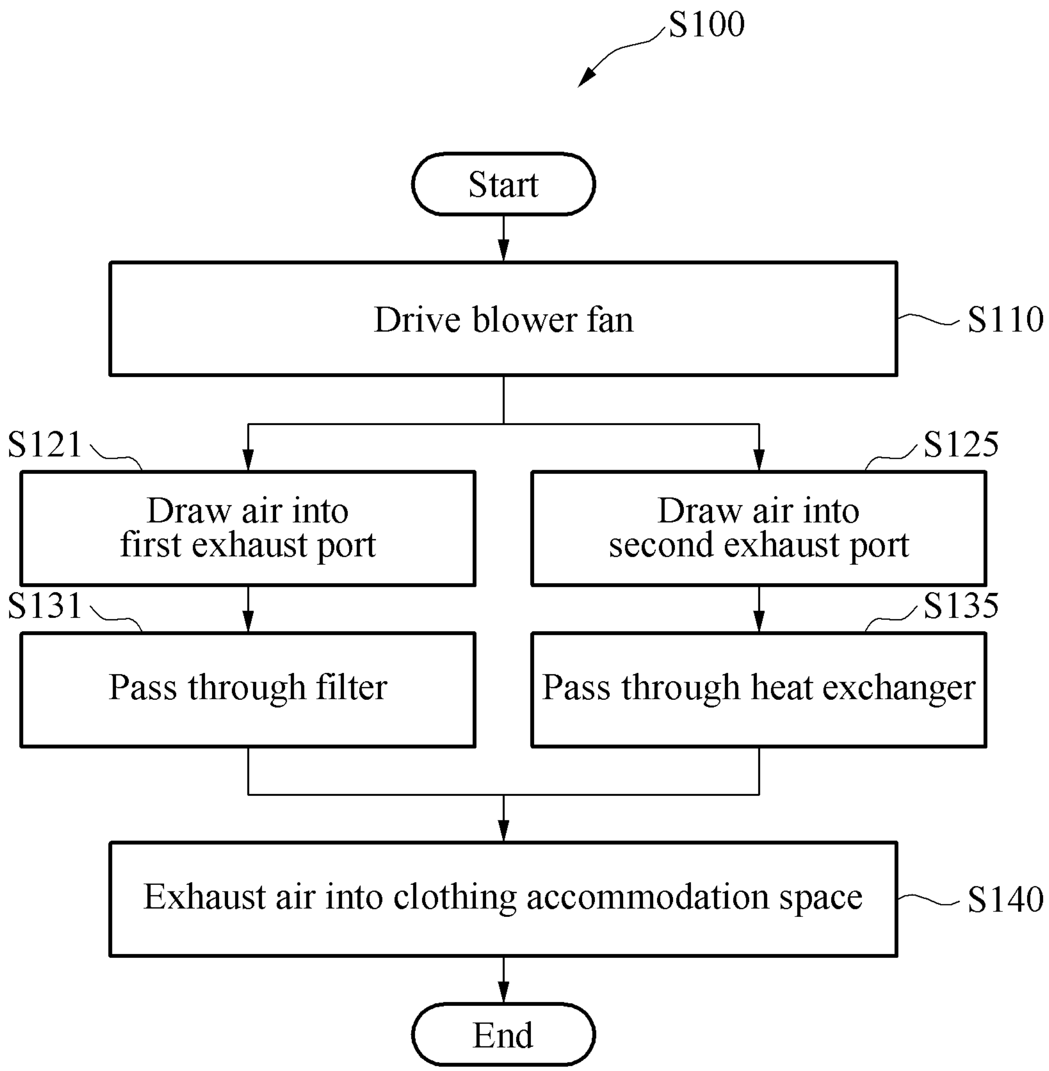
FIG. 7 is a flowchart illustrating a method of controlling a clothing management apparatus according to an embodiment of the present disclosure.

FIG. 7 is a flowchart illustrating a method S100 of controlling a clothing management apparatus according to an embodiment of the present disclosure.

Referring to FIG. 7, the method S100 of controlling the clothing management apparatus according to an embodiment may include at least some of the following operations or operations: operation S110 of driving the blower fan 113; operations S121 and S125 of drawing air into the first exhaust port 211 and the second exhaust port 221; and operation S140 of exhausting air into the clothing accommodation space 51.

In an embodiment, the method S100 of controlling the clothing management apparatus may be implemented with a combination of one or more configurations or features of the previously described embodiments of the clothing management apparatus 100, unless it is technically obviously impossible.

In describing the method S100 of controlling the clothing management apparatus, what has been described above about the clothing management apparatus 100 will not be repeated here, but various operations performed when the clothing management apparatus 100 is driven by at least one processor 130 or the user will be described below. However, the clothing management apparatus 100 on which the method S100 is performed is not limited to the preceding description, and the steps or operations described below may also be applied to the clothing management apparatus 100 of various types that may perform at least some of the following steps or operations.

In an embodiment, operation S110 of driving the blower fan 113 may drive the blower fan 113 to exhaust air into the clothing accommodation space 51. When the blower fan 113 is driven, air in the flow path assembly 114 may be exhausted into the clothing accommodation space 51, and an air flow may thereby be generated inside the clothing management apparatus 100 and the air inside the clothing management apparatus 100 may be circulated through the flow path assembly 114.

In an embodiment, operation S121 of drawing air into the first exhaust port 211 and operation S122 of drawing air into the second exhaust port 221 may draw air from the clothing accommodation space 51 into the first exhaust port 211 and the second exhaust port 221, separately. For example, the first exhaust port 211 and the second exhaust port 221 may be spaced apart from each other in the clothing accommodation space 51, and at least a portion of the air in the clothing accommodation space 51 may move into the first exhaust port 211 and the remainder of the air may move into the second exhaust port 221.

In an embodiment, operation S313 of passing through the filter 212 may allow air entering the first exhaust port 211 to pass through the filter 212 installed in the first exhaust flow path 210 communicating with the first exhaust port 211 to allow the filter 212 to collect dust generated in the inner case 50. Operation S131 of passing through the filter 212 may be an operation that is passively performed by operation S121 of drawing air into the first exhaust port 211. Alternatively, operation S313 of passing through the filter 212 may be an operation of moving a position of the filter 212 in the first exhaust flow path 210 by a separate control operation or an operation of changing a direction of an air flow and guiding air into the filter 212 by a separate control operation.

In an embodiment, in operation S313 of passing through the filter 212, the air that has passed through the first exhaust flow path 210 may bypass the heat exchanger 118 to be directed to the blower fan 113. The first exhaust port 211 and the second exhaust port 221 may be separated or partitioned from each other to draw air from the clothing accommodation space 51, and the air discharged through the second exhaust port 221 may pass through the heat exchanger 118 to be directed to the blower fan 113.

In an embodiment, operation S135 of passing through the heat exchanger 118 may allow air entering the second exhaust port 221 to pass through the heat exchanger 118 installed in the second exhaust flow path 220 communicating with the second exhaust port 221 to be heated therein. Operation S135 of passing through the heat exchanger 118 may be an operation that is passively performed by operation S125 of drawing air into the second exhaust port 221. Alternatively, operation S135 of passing through the heat exchanger 118 may be an operation of driving the heat exchanger 118 by a separate control operation or an operation of changing a direction of an air flow and guiding air into the heat exchanger 118 by a separate control operation.

In an embodiment, operation S140 of exhausting air into the clothing accommodation space 51 may receive air from the first exhaust flow path 210 and the second exhaust flow path 220 and guide the air to the blower fan 113 to exhaust the air into the clothing accommodation space 51. The air that has passed through the first exhaust flow path 210 and the second exhaust flow path 220 may be dusted off, heated, and guided to the circulation flow path 230, and may be discharged back into the clothing accommodation space 51 through the circulation flow path 230.

In an embodiment, the method S100 of controlling the clothing management apparatus may divide the air discharged into the clothing accommodation space 51 through an air flow generated by the blower fan 113 to be transferred to the first exhaust port 211 and the second exhaust port 221, separately. The air divided into the first exhaust port 211 and the second exhaust port 221 may be dusted off or heated to be transferred back to the clothing accommodation space 51, allowing the air inside the clothing management apparatus 100 to circulate, remove dust, wrinkles, or odors from the clothes C, and dry and sanitize the clothes C while circulating therein.

Figure 8:
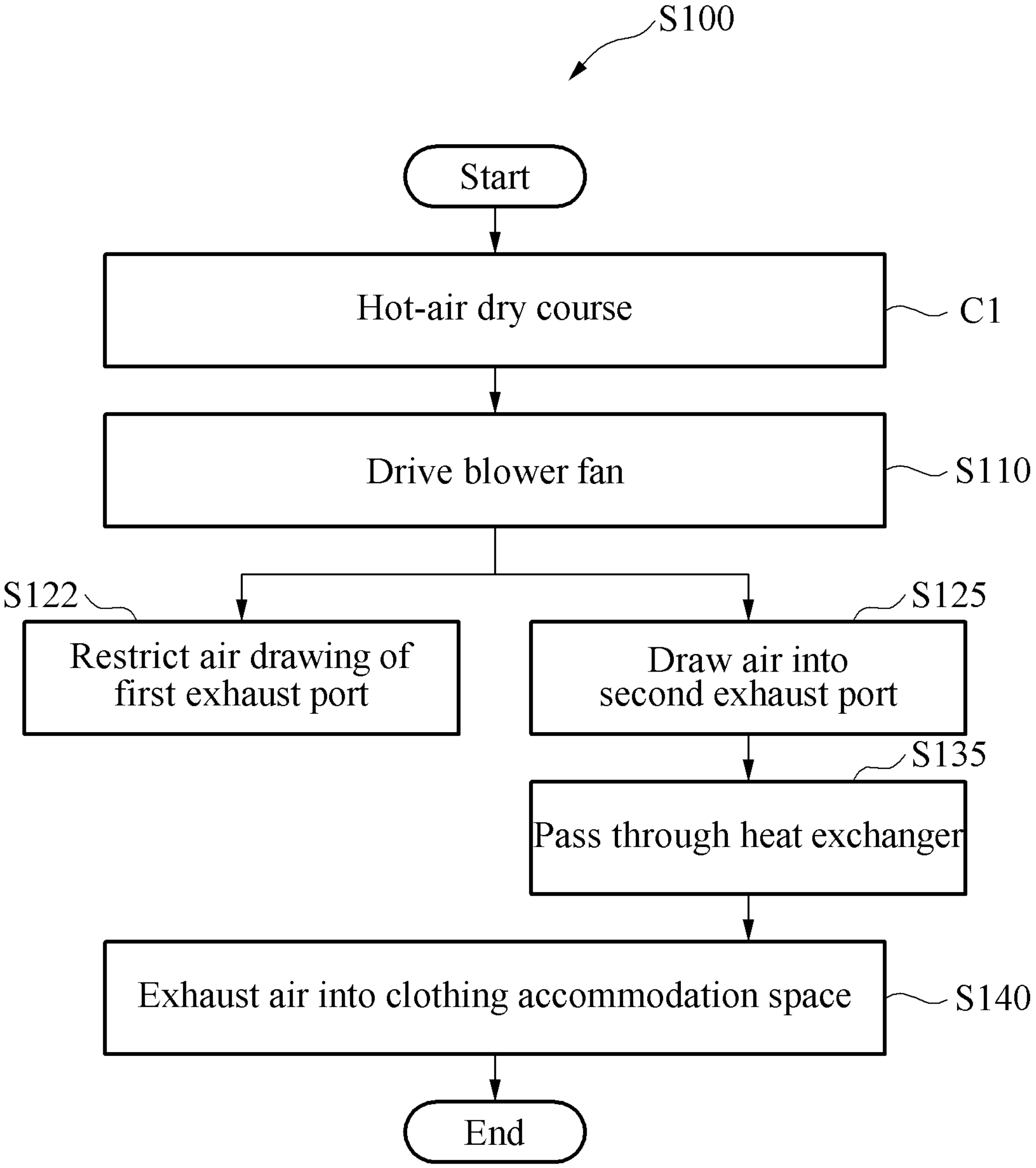
FIG. 8 is a flowchart illustrating a method of controlling a clothing management apparatus according to an embodiment of the present disclosure.

FIG. 8 is a flowchart illustrating a method S100 of controlling a clothing management apparatus according to an embodiment of the present disclosure.

Referring to FIG. 8, the method S100 of controlling the clothing management apparatus according to an embodiment may include a hot-air dry course C1.

In an embodiment, the method S100 of controlling the clothing management apparatus may be implemented by the clothing management apparatus 100 and/or with a combination of one or more configurations or features of the previously described embodiments of the clothing management apparatus 100, unless it is technically obviously impossible.

In an embodiment, the clothing management apparatus 100 may sequentially, or selectively, perform a plurality of courses to manage the clothes C. In an embodiment, the plurality of courses may be determined by various factors, such as, for example, a state or condition of the clothes C, an algorithm stored in the memory 170, or a user input, and at least one processor 130 may control the driving of a driving unit (e.g., the driving unit 110 in FIG. 2) to perform each course based on the factors.

In an embodiment, various operations of performing the plurality of courses may include the same or similar operations as at least some of the operations described above with reference to FIG. 7, and what has been described above will not be repeated below with reference to FIGS. 8 to 11.

In an embodiment, the hot-air dry course C1 may be a course for providing heated and dehumidified air to the clothes C to dry the wet clothes C, remove wrinkles or odors from the clothes C, or sanitize the clothes C.

In an embodiment, the method S100 of controlling the clothing management apparatus according to the hot-air dry course C1 may include at least some of the following steps or operations: operation S110 of driving the blower fan 113; operation S122 of restricting air drawing of the first exhaust port 211; and operation S125 of drawing air into the second exhaust port 221.

In an embodiment, when the hot-air dry course C1 is initiated, operation S110 of driving the blower fan 113 may be performed, and the blower fan 113 may induce air circulation in the flow path assembly 114 and the clothing accommodation space 51.

In an embodiment, operation S122 of restricting air drawing of the first exhaust port 211 may move the first damper unit 115*a* for controlling a flow volume of air entering the first exhaust port 211 to restrict air from being drawn into the first exhaust port 211. The first damper unit 115*a* may close the first exhaust port 211 or block an air flow in the first exhaust flow path 210. When the air drawing of the first exhaust port 211 is restricted, air in the clothing accommodation space 51 may be drawn into the second exhaust port 221.

In an embodiment, operation S125 of drawing air into the second exhaust port 221 may draw in a substantial majority of the air in the clothing accommodation space 51. Operation S135 of passing through the heat exchanger 118 may draw air from the clothing accommodation space 51 into the second exhaust port 221 and heat the air by the heat exchanger 118.

In an embodiment, operation S135 of passing through the heat exchanger 118 may increase a driving force of the heat exchanger 118 to heat and dehumidify a large volume of air. Operation S140 of exhausting air into the clothing accommodation space 51 may exhaust the heated and dehumidified hot dry air into the clothing accommodation space 51 to provide the hot air to the clothes C.

In an embodiment, the hot-air dry course C1 may substantially block air from being drawn into the first exhaust port 211, increase a flow volume of air drawn into the second exhaust port 221 or maintain a similar volume, and increase the temperature of air discharged through the air supply port 235.

Figure 9:
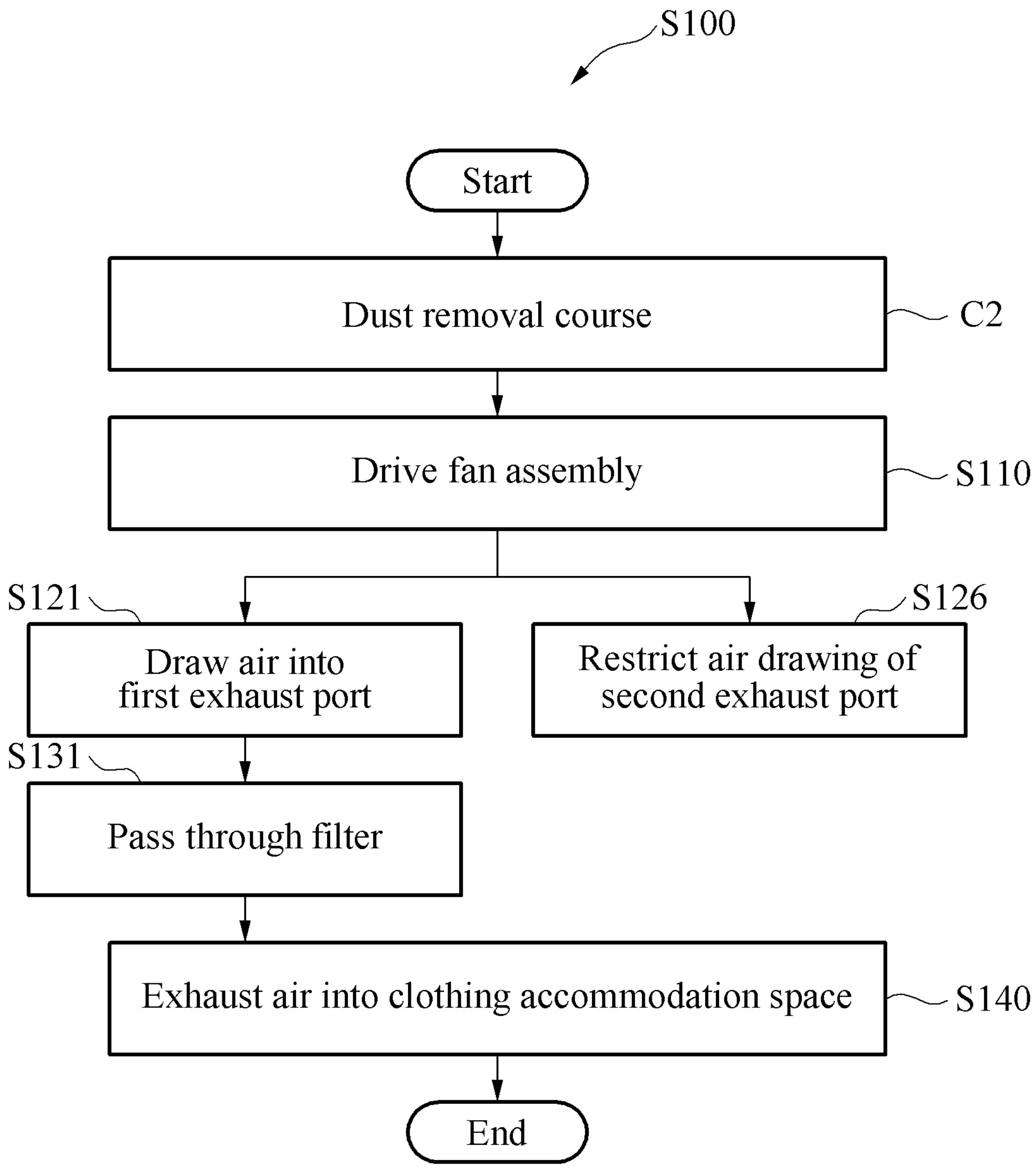
FIG. 9 is a flowchart illustrating a method of controlling a clothing management apparatus according to an embodiment of the present disclosure.

FIG. 9 is a flowchart illustrating a method S100 of controlling a clothing management apparatus according to an embodiment of the present disclosure.

Referring to FIG. 9, the method S100 of controlling the clothing management apparatus according to an embodiment may include a dust removal course C2.

In an embodiment, the method S100 of controlling the clothing management apparatus may be implemented by the clothing management apparatus 100 and/or with a combination of one or more configurations or features of the previously described embodiments of the clothing management apparatus 100, unless it is technically obviously impossible.

In an embodiment, the dust removal course C2 may be a driving course for intensively removing dust generated by the clothes C or an indoor air cleaning course for removing dust in an installation space, with the inner case 50 of the clothing management apparatus 100 open to the installation space of the clothing management apparatus 100.

In an embodiment, the method S100 of controlling the clothing management apparatus according to the dust removal course C2 may include at least some of the following steps or operations: operation S110 of driving the blower fan 113; S121 of drawing air into the first exhaust port 211; and operation S126 of restricting air drawing of the second exhaust port 221.

In an embodiment, when the dust removal course C2 is initiated, operation S110 of driving the blower fan 113 may be performed, and the blower fan 113 may induce air circulation in the flow path assembly 114 and the clothing accommodation space 51. When the blower fan 113 is driven, air discharged from the air supply port 235 may pass through or pressurize the clothes C, inducing any debris such as dust or fine dust remaining on the clothes C to fall off the clothes C.

In an embodiment, operation S126 of restricting air drawing of the second exhaust port 221 may move the second damper unit 115*b* for controlling a flow volume of air entering the second exhaust port 221 to restrict air from being drawn into the second exhaust port 221. The second damper unit 115*b* may close the second exhaust port 221 or block an air flow in the second exhaust flow path 220. When the air drawing of the second exhaust port 221 is restricted, air in the clothing accommodation space 51 may be drawn into the first exhaust port 211.

In an embodiment, operation S121 of drawing air into the first exhaust port 211 may draw in a substantial majority of the air in the clothing accommodation space 51. Operation S131 of passing through the filter 212 may draw air from the clothing accommodation space 51 into the first exhaust port 211 to allow the filter 212 to collect dust or fine dust. Operation S140 of exhausting air into the clothing accommodation space 51 may discharge the air free of dust into the clothing accommodation space 51 and induce dust remaining on the clothes C to fall off the clothes C.

In an embodiment, the dust removal course C2 may substantially block air from being drawn into the second exhaust port 221, increase a flow volume of air drawn into the first exhaust port 211 or maintain a similar volume, and reduce a contamination level of the air discharged through the air supply port 235.

Figure 10:
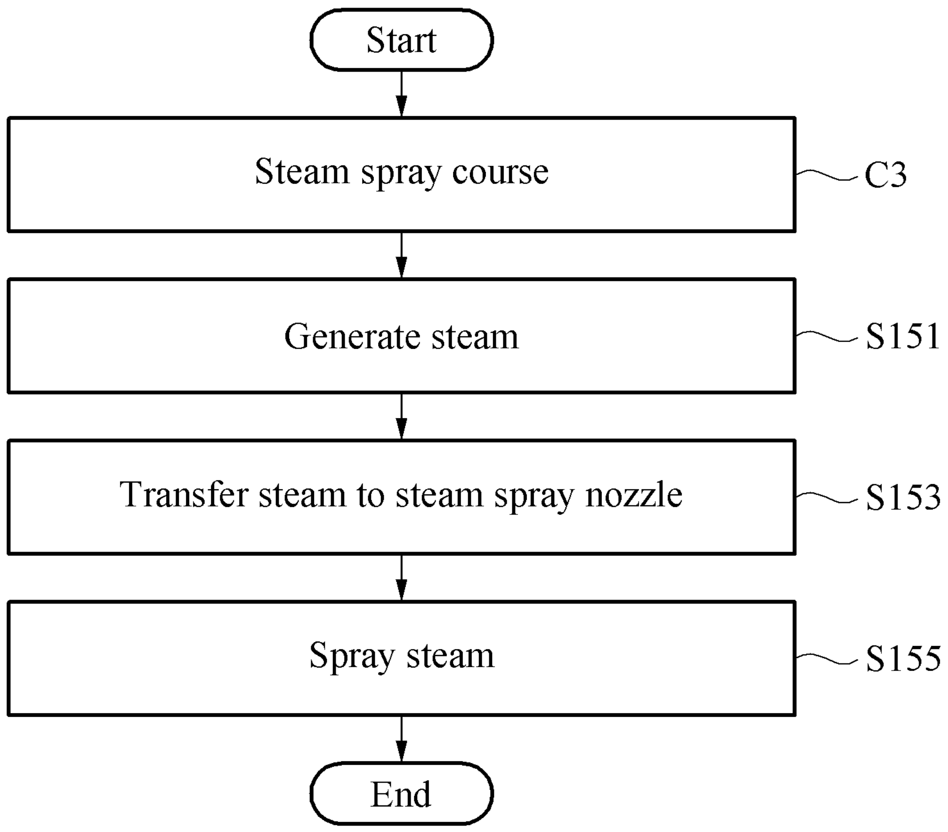
FIG. 10 is a flowchart illustrating a method of controlling a clothing management apparatus according to an embodiment of the present disclosure.

FIG. 10 is a flowchart illustrating a method S100 of controlling a clothing management apparatus according to an embodiment of the present disclosure.

Referring to FIG. 10, the method S100 of controlling the clothing management apparatus according to an embodiment may include a steam spray course C3.

In an embodiment, the method S100 of controlling the clothing management apparatus may be implemented by the clothing management apparatus 100 and/or with a combination of one or more configurations or features of the previously described embodiments of the clothing management apparatus 100, unless it is technically obviously impossible.

In an embodiment, the steam spray course C3 may be a course for spraying steam into the clothing accommodation space 51. In an embodiment, the method S100 of controlling the clothing management apparatus according to the steam spray course C3 may include at least some of the following steps or operations: operation S151 of generating steam; operation S153 of transferring steam to the steam spray nozzle 255; and operation S155 of spraying steam.

In an embodiment, operation S151 of generating steam may generate steam by the steam generation module 116 connected to the heat exchanger 118. The steam generation module 116 may receive water from the water reservoir 40 through the connection member 41, and allow the water to pass through the heat exchanger 118 or directly heat the water by a heater (not shown) to generate steam.

In an embodiment, operation S153 of transferring steam to the steam spray nozzle 255 may transfer the steam from the steam generation module 116 located in the second exhaust flow path 220 or the machine chamber 60 to the steam spray nozzle 255 located in the first exhaust flow path 210. Operation S155 of spraying steam may spray the steam received from the steam generation module 116 into the clothing accommodation space 51 by the steam spray nozzle 255.

In an embodiment, the steam spray course C3 may be a course in which a hot liquid is sprayed onto the clothes C to dissolve a contaminant, or the steam condenses and is released from the clothes C along with the contaminant, which may thus be performed when the clothes C is highly contaminated.

Figure 11:
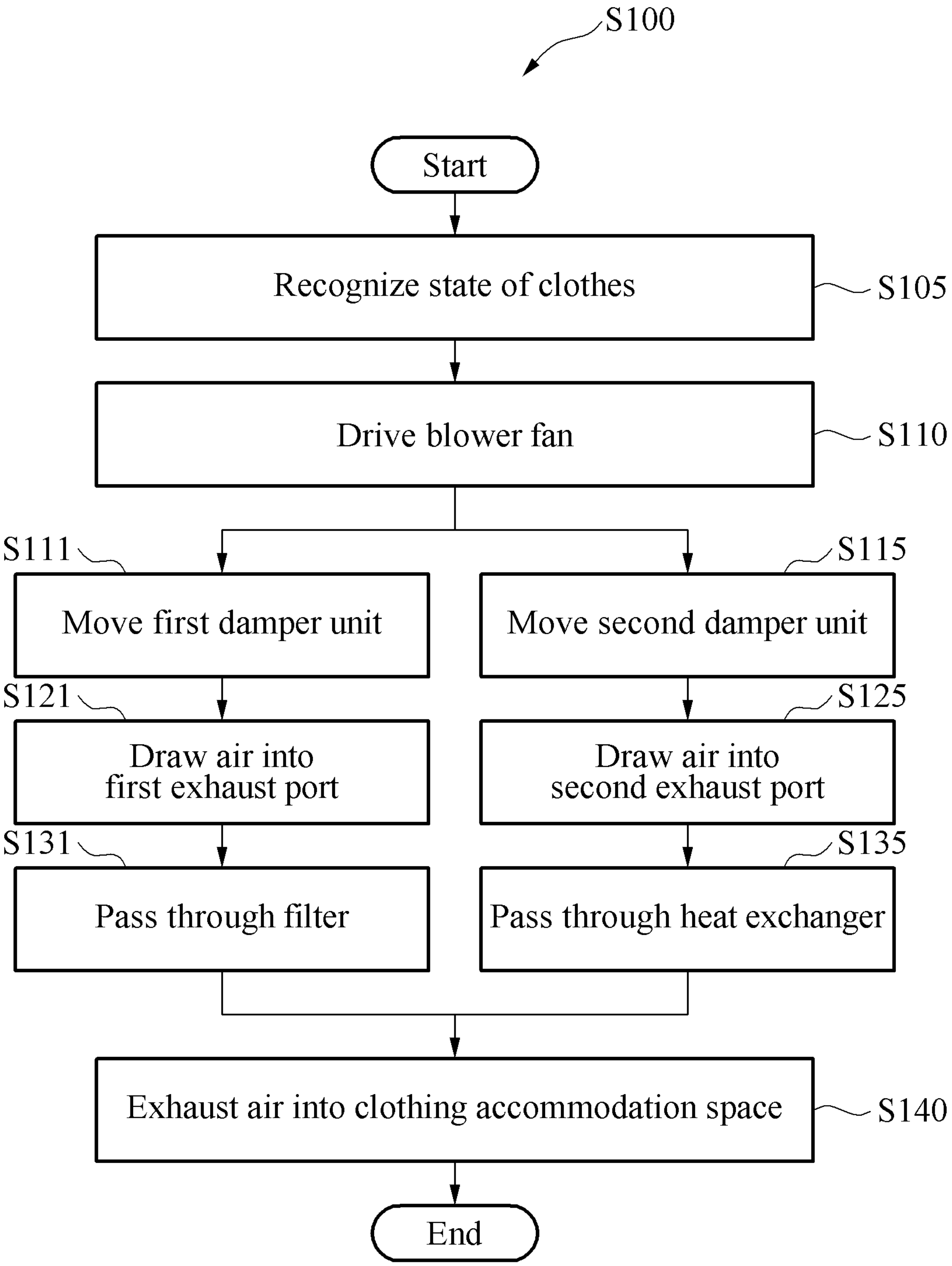
FIG. 11 is a flowchart illustrating a method of controlling a clothing management apparatus according to an embodiment of the present disclosure.

FIG. 11 is a flowchart illustrating a method S100 of controlling a clothing management apparatus according to an embodiment of the present disclosure.

Referring to FIG. 11, the method S100 of controlling the clothing management apparatus according to an embodiment may include at least some of the following steps or operations: operation S105 of recognizing a state of the clothes C; operation S111 of moving the first damper unit 115*a*; and operation S115 of moving the second damper unit 115*b*.

In an embodiment, the method S100 of controlling the clothing management apparatus may be implemented by the clothing management apparatus 100 and/or with a combination of one or more configurations or features of the previously described embodiments of the clothing management apparatus 100, unless it is technically obviously impossible.

In an embodiment, operation S105 of recognizing a state of the clothes C may recognize a state or condition of the clothes C accommodated in the inner case 50. In an embodiment, the method S100 of controlling the clothing management apparatus may control operations of the blower fan 113, the first damper unit 115*a*, and the second damper unit 115*b* based on information recognized in operation S105 of recognizing a state of the clothes C.

For example, the gas sensor 123 or the dust sensor 126 of the sensor module 120 may measure the concentration of gas or the concentration of dust in the inner case 50 in a state where the clothes C is accommodated, and may measure a contamination level of the air in the inner case 50 based on the measurements.

For example, operation S105 of recognizing a state of the clothes C may be an operation in which the user inputs the condition of the clothes C via the input module 150 and at least one processor 130 receives this input.

For example, operation S105 of recognizing a state of the clothes C may be an operation of receiving information about the surrounding environment including, for example, various sources of contamination of the clothes C, such as, a fine dust level, an ultra-fine dust level, or weather, within a movement radius of the user, via the communication module 150, or of receiving information related to the clothes C from an Internet of things (IoT) device.

In an embodiment, operation S110 of driving the blower fan 113 may control a driving force of the blower fan 113 based on the information recognized in operation S105 of recognizing a state of the clothes C. When the clothes C is recognized as highly contaminated, the driving force of the blower fan 113 may be increased to increase the pressure of air to be exhausted to the clothes C.

In an embodiment, operation S111 of moving the first damper unit 115*a* may move the first damper unit 115*a* for controlling a flow volume of air entering the first exhaust port 211 to adjust a flow volume ratio of air entering the first exhaust port 211. In an embodiment, S115 of moving the second damper unit 115*b* may move the second damper unit 115*b* for controlling a flow volume of air entering the second exhaust port 221 to adjust a flow volume ratio of air entering the second exhaust port 221.

In an embodiment, the method S100 of controlling the clothing management apparatus may perform operation S111 of moving the first damper unit 115*a* and S115 of moving the second damper unit 115*b*, based on the information recognized in operation S105 of recognizing a state of the clothes C to control a flow volume of air passing through the first exhaust port 211 and the second exhaust port 221.

For example, when the first damper unit 115*a* moves to close the first exhaust port 211, it may correspond to operation S122 of restricting air drawing of the first exhaust port 211 described above with reference to FIG. 8, and when the second damper unit 115*b* moves to close the second exhaust port 221, it may correspond to operation S126 of restricting air drawing of the second exhaust port 221 described above with reference to FIG. 9.

In an embodiment, at least one processor 130 may periodically receive, via the sensor module 120, information about a state or condition of air in the clothing accommodation space 51, such as, a contamination level of the air, the temperature of the air, or the humidity of the air, and may control a flow volume of air transferred to the first exhaust port 211 and the second exhaust port 221 based on the information.

For example, when the dust sensor 126 recognizes that the clothes C is less dusty, or the humidity sensor 121 recognizes that the clothes C is wet, at least one processor 130 may control the damper module 115 to decrease a flow volume of air passing through the first exhaust port 211 and increase a flow volume of air passing through the second exhaust port 221.

For example, when the dust sensor 126 recognizes that the clothes C is dusty, or the humidity sensor 121 recognizes that the clothes C is dry, at least one processor 130 may control the damper module 115 to decrease a flow volume of air passing through the second exhaust port 221 and increase a flow volume of air passing through the first exhaust port 211.

According to an embodiment, a clothing management apparatus 100 may include: an outer case 10 forming an exterior; an inner case 50 disposed inside the outer case 10 and forming a clothing accommodation space 51; a heat exchanger 118 disposed below a bottom surface 50*a* of the inner case 50; and a blower fan 113 disposed between the outer case 10 and the inner case 50 and adapted to induce an air flow, wherein the inner case 50 may include: an air supply port 235 disposed on a top surface 50*c* of the inner case and adapted to supply air to the clothing accommodation space 51; a first exhaust port 211 disposed on a side surface 50*b* between the bottom surface 50*a* and the top surface 50*c* of the inner case 50; and a second exhaust port 221 disposed on the bottom surface 50*a* of the inner case 50, wherein air discharged through the first exhaust port 211 may bypass the heat exchanger 118 to be directed toward the blower fan 113, and air discharged through the second exhaust port 221 may pass through the heat exchanger 118 to be directed toward the blower fan 113.

In an embodiment, the first exhaust port 211 may be open to be inclined at a predetermined angle in a direction from the bottom surface 50*a* of the inner case 50 to the side surface 50*b* to draw air from the clothing accommodation space 51.

In an embodiment, the first exhaust port 211 may be open in a direction substantially parallel to the side surface 50*b* to draw air from the clothing accommodation space 51.

In an embodiment, the second exhaust port 221 may be open in a direction substantially parallel to the bottom surface 50*a* to draw air from the clothing accommodation space 51.

In an embodiment, the clothing management apparatus 100 may include a circulation flow path 230 formed between the side surface 50*b* and the outer case 10 and adapted to receive air from the first exhaust port 211 and the second exhaust port 221 and transfer the air to the air supply port 235.

In an embodiment, the blower fan 113 may be disposed inside the circulation flow path 230 to induce air circulation between the clothing accommodation space 51 and the circulation flow path 230.

In an embodiment, the clothing management apparatus 100 may include a first exhaust flow path 210 adapted to guide air drawn into the first exhaust port 211 into the circulation flow path 230; and a second exhaust flow path 220 adapted to guide air drawn into the second exhaust port 221 into the circulation flow path 230.

In an embodiment, the first exhaust flow path 210 may be directly communicate with the circulation flow path 230, and the second exhaust flow path 220 may communicate with the circulation flow path 230 via the first exhaust flow path 210.

In an embodiment, the clothing management apparatus 100 may include a filter 212 disposed in the first exhaust port 211 and adapted to collect dust from air drawn into the first exhaust port 211.

In an embodiment, the clothing management apparatus 100 may include a steam generation module 116 adapted to generate steam; a steam spray hole 251 formed in the inner case 50 to spray steam into the clothing accommodation space 51; and a steam spray nozzle 255 adapted to receive steam from the steam generation module 116 and spray the steam into the inner case 50 through the steam spray hole 251.

In an embodiment, the steam spray hole 251 may be formed on the first exhaust port 211, on the side surface 50*b* of the inner case 50.

In an embodiment, the clothing management apparatus 100 may include a first damper unit 115*a* that is movable to control a flow volume of air entering the first exhaust port 211.

In an embodiment, the clothing management apparatus 100 may include a second damper unit 115*b* that is moveable to control a flow volume of air entering the second exhaust port 221.

In an embodiment, the clothing management apparatus 100 may include at least one processor 130 configured to control an operation of the clothing management apparatus 100 to perform a plurality of courses, wherein at least one processor 130 may be configured to: control a movement of the first damper unit 115*a* and the second damper unit 115*b* to regulate a flow volume ratio between the air entering the first exhaust port 211 and the air entering the second exhaust port 221, based on the plurality of courses.

According to an embodiment, a method S100 of controlling a clothing management apparatus 100 including an outer case 10, an inner case 50 disposed inside the outer case 10 to form a clothing accommodation space 51, a blower fan 113 installed between the outer case 10 and the inner case 50 to induce an air flow, and a first exhaust port 211 and a second exhaust port 221 that are open to the inner case 50, the method S100 including: operation S110 of driving the blower fan 113 to discharge air into the clothing accommodation space 51; operations S121 and S125 of dividing and discharging air from the clothing accommodation space to the first exhaust port and the second exhaust port, separately; operation S131 of collecting dust generated in the inner case 50 as air drawn into the first exhaust port 211 passes through a filter 212 installed in a first exhaust flow path 210 communicating with the first exhaust port 211; operation S135 of heating air drawn into the second exhaust port 221 as the air passes through a heat exchanger 118 installed in a second exhaust flow path 220 communicating with the second exhaust port 221; and operation S140 of receiving air from the first exhaust port 211 and the second exhaust port 221 and guiding the air to the blower fan 113 to exhaust the air into the inner case 50, wherein, during operation S131 of collecting dust, air passing through the first exhaust flow path 210 may bypass the heat exchanger 118 to be directed toward the blower fan 113.

In an embodiment, the method S100 of controlling the clothing management apparatus 100 may include a hot-air dry course C1. The hot-air dry course C1 may include: operation S122 of moving a first damper unit 115*a* that controls a flow volume of air entering the first exhaust port 211 to restrict air from being drawn into first exhaust port 211; and operations S125 and S135 of drawing air from the inner case 50 into the second exhaust port 221 to allow the heat exchanger 118 to heat the air.

In an embodiment, the method S100 of controlling the clothing management apparatus 100 may include a dust removal course C2. The dust removal course C2 may include: operation S126 of moving a second damper unit 115*b* that controls a flow volume of air entering the second exhaust port 221 to restrict air from being drawn into the second exhaust port 221; and operations S121 and S131 of drawing air from the inner case 50 into the first exhaust port 211 to allow the filter 212 to collect dust.

In an embodiment, the method S100 of controlling the clothing management apparatus 100 may include the dust removal course C2. The dust removal course C2 may include: operation S126 of moving the second damper unit 115*b* that controls a flow volume of air entering the second exhaust port 221 to restrict air from being drawn into the second exhaust port 221; and operations S121 and S131 of drawing air from the clothing accommodation space 51 into the first exhaust port 211 to allow the filter 212 to collect dust.

In an embodiment, the method S100 of controlling the clothing management apparatus 100 may include a steam spray course C3. The steam spray course C3 may include: operation S151 of generating steam by a steam generation module 116 connected to the heat exchanger 118; and operations S153 and S155 of spraying steam into the clothing accommodation space 51 by a steam spray nozzle 255 receiving the steam from the steam generation module 116.

In an embodiment, the method S100 of controlling the clothing management apparatus 100 may include operations S111 and S115 of moving the first damper unit 115*a* adapted to control a flow volume of air entering the first exhaust port 211 and the second damper unit 115*b* adapted to control a flow volume of air entering the second exhaust port 221, to regulate a flow volume ratio between the air entering the first exhaust port 211 and the air entering the second exhaust port 221.

In an embodiment, the method S100 of controlling the clothing management apparatus 100 may include operation S105 of recognizing a state of clothes received in the inner case 50, and controlling operations of the blower fan 113, the first damper unit 115*a*, and the second damper unit 115*b* based on recognized information.

In an embodiment, the method S100 of controlling the clothing management apparatus 100 may include the steam spray course C3. The steam spray course C3 may include: operation S151 of generating steam by the steam generation module 116 connected to the heat exchanger 118; and operations S153 and S155 of spraying steam into the inner case 50 by the steam spray nozzle 255 receiving the steam from the steam generation module 116.

In an embodiment, the method S100 of controlling the clothing management apparatus 100 may include operations S111 and S115 of moving the first damper unit 115*a* adapted to control a flow volume of air entering the first exhaust port 211 and the second damper unit 115*b* adapted to control a flow volume of air entering the second exhaust port 221, to regulate a flow volume ratio between the air entering the first exhaust port 211 and the air entering the second exhaust port 221.

In an embodiment, the method S100 of controlling the clothing management apparatus 100 may include operation S105 of recognizing a state of clothes received in the inner case 50, and controlling operations of the blower fan 113, the first damper unit 115*a*, and the second damper unit 115*b* based on recognized information.

While the disclosure has been shown and described with reference to various embodiments thereof, it will be understood that the various embodiments are intended to be illustrative, not limiting. It will further be understood by those skilled in the art that various changes in form and details may be made without departing from the true spirit and full scope of the disclosure as defined by the appended claims and their equivalents.

What is claimed is:

1. A clothing management apparatus, comprising:
- an outer case forming an exterior of the clothing management apparatus;
- an inner case, arrangeable inside the outer case, to thereby form a clothing accommodation space;
- a heat exchanger arrangeable below a bottom surface of the inner case; and
- a fan, arrangeable between the outer case and the inner case, and the fan induces an air flow inside the clothing accommodation space,
- wherein the inner case comprises:
  - an air supply port, arrangeable on a top surface of the inner case, and the air flow is introduced to the clothing accommodation space through the air supply port;
  - a first exhaust port, arrangeable on a side surface of the inner case between the bottom surface of the inner case and the top surface of the inner case; and
  - a second exhaust port, arrangeable on the bottom surface of the inner case,
  - wherein air introduced through the first exhaust port is discharged bypassing the heat exchanger and directed toward the fan, and air introduced through the second exhaust port is discharged passing through the heat exchanger and directed toward the fan.

2. The clothing management apparatus of claim 1, wherein the first exhaust port is open to be inclined at a predetermined angle in a direction from the bottom surface of the inner case to the side surface to draw air from the clothing accommodation space.

3. The clothing management apparatus of claim 1, wherein the first exhaust port is open in a direction substantially parallel to the side surface to draw air from the clothing accommodation space.

4. The clothing management apparatus of claim 1, wherein the second exhaust port is open in a direction substantially parallel to the bottom surface to draw air from the clothing accommodation space.

5. The clothing management apparatus of claim 1, comprising:
- a circulation flow path formed between the side surface and the outer case to receive air from the first exhaust port and the second exhaust port and transfer the air to the air supply port.

6. The clothing management apparatus of claim 5, wherein the fan is arrangeable inside the circulation flow path to induce air circulation between the clothing accommodation space and the circulation flow path.

7. The clothing management apparatus of claim 5, comprising:
- a first exhaust flow path to guide air drawn into the first exhaust port into the circulation flow path; and
- a second exhaust flow path to guide air drawn into the second exhaust port into the circulation flow path.

8. The clothing management apparatus of claim 7, wherein the first exhaust flow path directly communicates with the circulation flow path, and
- the second exhaust flow path communicates with the circulation flow path via the first exhaust flow path.

9. The clothing management apparatus of claim 1, comprising:
- a filter arrangeable in the first exhaust port to collect dust from air drawn into the first exhaust port.

10. The clothing management apparatus of claim 1, comprising:
- a steam generation module to generate steam;
- a steam spray hole formed in the inner case to spray steam into the clothing accommodation space; and
- a steam spray nozzle to receive steam from the steam generation module and spray the steam into the inner case through the steam spray hole.

11. The clothing management apparatus of claim 10, wherein the steam spray hole is formed on the first exhaust port, on the side surface of the inner case.

12. The clothing management apparatus of claim 1, comprising:
- a first damper unit that is movable to control a flow volume of the air introduced through the first exhaust port.

13. The clothing management apparatus of claim 12, comprising:
- a second damper unit that is movable to control a flow volume of the air introduced through the second exhaust port.

14. The clothing management apparatus of claim 13, comprising:
- at least one processor configured to control an operation of the clothing management apparatus to perform a plurality of courses,
- wherein the at least one processor is configured to
  - control a movement of the first damper unit and the second damper unit to regulate a flow volume ratio between the air introduced through the first exhaust port and the air introduced through the second exhaust port, based on the plurality of courses.

15. A method of controlling a clothing management apparatus, the method comprising:
- driving a fan, arrangeable between an outer case of the clothing management apparatus and an inner case inside the outer case, to introduce air into a clothing accommodation space formed by the inner case;
- guiding the air from the clothing accommodation space to introduce through the air to a first exhaust port and introduce the air through a second exhaust port, respectively;
- collecting dust generated in the inner case as the air is introduced through the first exhaust port such that the air passes through a filter arrangeable along a first exhaust flow path, the first exhaust port being along the first exhaust flow path;
- heating the air introduced through the second exhaust port as the air passes through a heat exchanger arrangeable along a second exhaust flow path, the second exhaust port being along the second exhaust flow path; and receiving air from the first exhaust port and the second exhaust port and guiding the air to the fan to exhaust the air into the inner case, wherein, during the collecting of the dust, air passing through the first exhaust flow path bypasses the heat exchanger and is directed toward the fan.

16. The method of claim 15, comprising a hot-air dry course, wherein the hot-air dry course comprises:

moving a first damper unit that controls a flow volume of the air introduced through the first exhaust port to restrict air from being introduced into the first exhaust port; and drawing air from the inner case into the second exhaust port to allow the heat exchanger to heat the air.

17. The method of claim 15, comprising a dust removal course, wherein the dust removal course comprises:

moving a second damper unit that controls a flow volume of the air introduced through the second exhaust port to restrict air from being introduced into the second exhaust port; and drawing air from the inner case into the first exhaust port to allow the filter to collect dust.

18. The method of claim 15, comprising a steam spray course, wherein the steam spray course comprises:

generating steam by a steam generation module connected to the heat exchanger; and spraying steam into the inner case by a steam spray nozzle receiving the steam from the steam generation module.

19. The method of claim 15, comprising:

moving a first damper unit to control a flow volume of the air introduced through the first exhaust port and moving a second damper unit to control a flow volume of the air introduced through the second exhaust port, to regulate a flow volume ratio between the air through the first exhaust port and the air through the second exhaust port.

20. The method of claim 19, comprising:

recognizing a state of clothes received in the inner case, and controlling operations of the fan, the first damper unit, and the second damper unit based on recognized information.

* * * * *